United States Patent
Lavaud et al.

(10) Patent No.: US 10,960,042 B2
(45) Date of Patent: Mar. 30, 2021

(54) EUTECTIC EXTRACTION SOLVENTS, EXTRACTION METHODS BY EUTECTIGENESIS USING SAID SOLVENTS, AND EXTRACTS DERIVED FROM SAID EXTRACTION METHODS

(71) Applicants: NATUREX, Avignon (FR); UNIVERSITE D'AVIGNON ET DES PAYS DE VAUCLUSE, Avignon (FR)

(72) Inventors: Alexis Lavaud, Sorgues (FR); Michael Laguerre, Montfavet (FR); Simona Birtic, Cavaillon (FR); Anne Sylvie Fabiano Tixier, Rochefort du Gard (FR); Marc Roller, Morieres les Avignon (FR); Farid Chemat, Morieres les Avignon (FR); Antoine Charles Bily, Vedene (FR)

(73) Assignees: UNIVERSITE D'AVIGNON ET DES PAY DE VAUCLUSE, Avignon (FR); NATUREX, Avignon (FR)

( * ) Notice: Subject to any disclaimer, the term of this patent is extended or adjusted under 35 U.S.C. 154(b) by 0 days.

(21) Appl. No.: 15/564,985

(22) PCT Filed: Apr. 11, 2016

(86) PCT No.: PCT/GB2016/051014
§ 371 (c)(1),
(2) Date: Oct. 6, 2017

(87) PCT Pub. No.: WO2016/162703
PCT Pub. Date: Oct. 13, 2016

(65) Prior Publication Data
US 2018/0055904 A1 Mar. 1, 2018

(30) Foreign Application Priority Data

Apr. 10, 2015 (FR) .................................. 1553092
Dec. 8, 2015 (FR) .................................. 1562033

(51) Int. Cl.
| | | |
|---|---|---|
| *A61K 36/00* | (2006.01) | |
| *A61K 36/736* | (2006.01) | |
| *B01D 11/02* | (2006.01) | |
| *A61K 36/53* | (2006.01) | |
| *A61K 36/63* | (2006.01) | |
| *A23L 33/105* | (2016.01) | |
| *A61K 36/11* | (2006.01) | |
| *A61K 36/23* | (2006.01) | |
| *A61K 36/31* | (2006.01) | |
| *A61K 36/88* | (2006.01) | |

(52) U.S. Cl.
CPC .......... *A61K 36/736* (2013.01); *A23L 33/105* (2016.08); *A61K 36/11* (2013.01); *A61K 36/23* (2013.01); *A61K 36/31* (2013.01); *A61K 36/53* (2013.01); *A61K 36/63* (2013.01); *A61K 36/88* (2013.01); *B01D 11/02* (2013.01); *B01D 11/0288* (2013.01); *A61K 2236/331* (2013.01)

(58) Field of Classification Search
None
See application file for complete search history.

(56) References Cited

U.S. PATENT DOCUMENTS

| | | | |
|---|---|---|---|
| 7,183,433 B2 | 2/2007 | Abbott et al. | |
| 2016/0242442 A1* | 8/2016 | Kraehenbuehl | ........ A23L 27/201 |
| 2016/0242445 A1* | 8/2016 | Oertling | ................... A21D 2/14 |

FOREIGN PATENT DOCUMENTS

| | | |
|---|---|---|
| EP | 1324979 B1 | 11/2006 |
| WO | 2011/155829 A1 | 12/2011 |
| WO | 2012/145522 A2 | 10/2012 |
| WO | 2015/044139 A1 | 4/2015 |
| WO | WO-2015044136 A1 * | 4/2015 ............. A23L 2/201 |

OTHER PUBLICATIONS

Dai et al. (2013) Analytica Chimica Acta 766: 61-68. (Year: 2013).*
Duan et al. (2016) ACS Sustainable Chem. Eng. 4, 2405-2411. (Year: 2016).*
Vanda et al. (2018) C. R. Chinnie 21: 628-638. (Year: 2018).*
Khodaverdian et al. (2018) Intern. J. Biol. Macromolecules, vol. 107, Part B: 2574-2579. (Year: 2018).*
Paiva et al. (2014) ACS Sustainable Chem. Eng. 2, 1063-1071 (Year: 2014).*
Raskin et al. (2004) Current Pharmaceutical Design, 10, 3419-3429. (Year: 2004).*
Revilla et al. (1998) J. Agric. Food Chem. 46, 4592-4597. (Year: 1998).*
Dai et al., "Natural Deep Eutectic Solvents as New Potential Media for Green Technology," Analytica Chimica Acta 766:61-68 (2013).
Cardellini et al., "Novel Zwitterionic Deep Eutectic Solvents from Trimethylglycine and Carboxylic Acids: Characterization of their Properties and their Toxicity," RSC Adv. 4(99):55900-56002 (2014).
PCT International Search Report and Written Opinion corresponding to PCT/GB2016/051014, dated Sep. 2, 2016.
Craig, Stuart AS, "Betaine in Human Nutrition," Am J Clin Nutr 80:539-549 (2004).
Choi et al., "Are Natural Deep Eutectic Solvents the Missing Link in Understanding Cellular Metabolism and Physiology?," Plant Physiology 156:1701-1705 (2011).
Abbott et al., "Novel Solvent Properties of Choline Chloride/Urea Mixtures," Chem. Commun. 70-71 (2003).
Guitierrez et al., "Freeze-Drying of Aqueous Solutions of Deep Eutectic Solvents: A Suitable Approach to Deep Eutectic Suspensions of Self-Assembled Structures," Langmuir 25(10):5509-5515 (2009).

(Continued)

*Primary Examiner* — Russell G Fiebig
(74) *Attorney, Agent, or Firm* — Troutman Pepper Hamilton Sanders LLP

(57) ABSTRACT

A eutectic extraction solvent for extracting plant (e.g. vegetable) and/or animal and/or prokaryotic biological material, wherein the solvent is a clear, stable and fluid mixture comprising: (a) betaine or a hydrated form of betaine; (b) at least one hydrogen bond donor compound selected from the group consisting of polyols and organic acids; and (c) water with the proviso that the eutectic extraction solvent does not contain any exogenous sugar and/or amine salt and/or anion.

14 Claims, 24 Drawing Sheets

(56) References Cited

OTHER PUBLICATIONS

Robinson, Jr. et al., Dicaffeoylquinic Acid Inhibitors of Human Immunodeficiency Virus Integrase: Inhibition of the Core Catalytic Domain of Human Immunodeficiency Virus Integrase, Molecular Pharmacology 50:846-855 (1996).

Ou et al., "Determination of Total Antioxidant Capacity by Oxygen Radical Absorbance Capacity (ORAC) Using Fluorescein as the Fluorescence Probe: First Action 2012.23," Journal of AOAC International 96(6)1372-1376 (2013).

Ou et al., "Development and Validation of an Improved Oxygen Radical Absorbance Capacity Assay Using Fluorescein as the Fluorescent Probe," J. Agric. Food Chemical 49:4619-4626 (2001).

Laguerre et al., "Characterization of Olive-Leaf Phenolics by ESI-MS and Evaluation of their Antioxidant Capacities by the CAT Assay," J Am Oil Chem Soc 86:1215-1225 (2009).

An et al., "Flavonoids, Taxifolin, and Luteolin Attenuate Cellular Melanogenesis Despite Increasing Tyrosinase Protein Levels," Phytother. Res. 22:1200-1207 (2008).

\* cited by examiner

EUTECTIC EXTRACTION SOLVENTS, EXTRACTION METHODS BY EUTECTIGENESIS USING SAID SOLVENTS, AND EXTRACTS DERIVED FROM SAID EXTRACTION METHODS

This application is a national stage application under 35 U.S.C. § 371 of PCT Application No. PCT/GB2016/051014, filed Apr. 11, 2016, which claims priority of France Patent Application Nos. 1553092, filed Apr. 10, 2015, and U.S. Pat. No. 1,562,033, filed Dec. 8, 2015.

FIELD OF THE INVENTION

In a general manner the present invention relates to:
- a eutectic solvent for extracting plant (e.g. vegetable) and/or animal and/or prokaryotic biological material;
- the use of said eutectic extraction solvent to put into effect a method for extracting natural biological compounds;
- a method for extracting natural biological compounds such as phenolic compounds, using said solvent;
- the natural biological liquid extract derived from the implementation of said extraction method; and
- the use of said natural biological liquid extract.

More particularly, implementation of the invention is made possible by a proportioned mixture of betaine (trimethyl glycine) or hydrated forms of betaine, at least one hydrogen bond donor selected from the group consisting of polyols and organic acids, and water, which is useful in providing improved extraction of natural compounds from the biological material used.

BACKGROUND OF THE INVENTION

Betaine is a trimethylated form of glycine discovered for the first time in sugar beet juice. By virtue of its structure and physico-chemical properties, this natural molecule is of particular interest in the cosmetics, pharmaceuticals, food and nutrition/health sectors. It is used in particular for its hydrating, emollient and moisturising properties in maintaining the water content of a cosmetic product, as well as in preserving an optimum moisture balance of the skin. This beneficial effect results from a particular positioning at the interface of human skin cells. In addition, betaine is a natural osmolyte which protects human cells—as it does cells—against osmotic stress. When ingested in the diet or by nutraceutical supplementation, this molecule plays a hepatic protective role by enabling sufficient methylation of certain liver enzymes. Conditions associated with the hepatic metabolism of lipids have also been identified as a result of insufficient intake of betaine which can lead to steatosis (Craig, S.A.S., Betaine in human nutrition, Am. J. Clin. Nutr., 2004, 80, 539-549).

Besides its physiological and technological role, betaine is inexpensive (~10 euros/kg), biologically sourced and non-toxic. It is a primary metabolite produced in considerable quantities during sugar beet processing for the production of saccharose, accounting for up to 30% of the molasses thus obtained. Given the industrial quantities involved, there remain stocks of betaine that have little or no development value. Deicing of roads with betaine-rich beet juice obtained after extracting the sugar is one of a number of examples of use of this compound in very low value-added sectors. New applications in niche markets are therefore sought after. Betaine is of undoubted value in the preparation of cocamidopropyl betaine used in the cosmetics industry as a surfactant, but this chemical product is derived from organic synthesis. In a context where artificiality is increasingly deprecated, this avenue of development appears to be more compromised than ever. Thus, societal, economic and regulatory changes driven by the desire of consumers to move towards more natural options have provided the impetus for the use of natural substances in environmentally friendly processes with low energy inputs (for example, low temperature).

A problem often encountered by the person skilled in the art is that of the high heat sensitivity of the molecules of interest, foremost among which are natural compounds containing aromatic cores substituted by hydroxyl groups (phenolic compounds, alcohols, phenolic acids and esters, flavonoids, tannins, stilbenes and phenolic terpenes). It is also known that the saccharidic portion of saponins and triterpenes as well as the associated conjugated systems of terpenes and carotenoids can be isomerised or oxidised beyond 60-70° C.

An essential characteristic of betaine is the combination of a quaternary ammonium group with a carboxylic acid, which are particularly well suited to solubilisation and to extraction of polar or amphiphilic substances, in particular by forming hydrogen and/or ionic bonds with the solute to be extracted. In an approach guided by the principles of green chemistry and eco-extraction, it would be advantageous to be able to use betaine both as active principle and as extracting fluid in a mixture with other constituents. However, it appears that there is no existing application of betaine for the extraction of natural substances of cosmetic, pharmaceutical or nutritional interest, such as phenolic compounds, antioxidants, saponins, carotenoids, terpenes or others, for the good reason that betaine exists in solid form at ambient temperature and is not amenable to the extraction of any natural substance due to its physical state.

Recent progress in chemistry shows, however, that a solid can be brought into the liquid state when it is formulated in a precise fashion in a mixture with one or more other specific compounds in suitable proportions. This applies in particular to deep eutectic solvents which are mixtures of compounds having melting points much lower than those of their constituents taken in isolation. They take their name from the Greek "eutektos" meaning "easily melted", a term which was used for the first time by the English physician Guthrie in 1884. These solvents, described by Abbott et al. in the document EP 1 324 979, are generally liquid at ambient temperature, whereas the compounds which the mixtures are composed of are solid compounds when considered separately. This phenomenon of lowering of melting points by the formation of a eutectic mixture is attributable to the establishment of inter-molecular hydrogen bonds, which have the effect of increasing the volume of the space between the chemical species thereby increasing their mobility such that they are rendered liquid.

In recent years particular attention has been given to the use of natural substances for inclusion in the composition of these eutectic solvents, which are then referred to as natural deep eutectic solvents (NADES). They are composed of organic acids, amino acids, sugars, polyols, choline and urea (Choi, Y. H., van Spronsen, J., Dai, Y., Verberne, M., Hollmann, F., Arends, I. W. C. E., Witkamp, G. J., Verpoorte, R., Are natural deep eutectic solvents the missing link in understanding cellular metabolism and physiology, Plant Physiol., 2011, 156, 1701-1705). These natural substances are ideal constituents for preparing eutectic mixtures by virtue of the fact that they are abundant in the biomass, they exhibit wide structural diversity, they are biodegradable, they exhibit low toxicity, they are edible for the most part, and they are natural. They are described in particular in the documents of the family WO 2011/55829.

However, these natural eutectic solvents have a certain number of drawbacks for industrial scale use. For example, the concomitant use of sugars and amino acids are known to the person skilled in the art to form odoriferous and coloured compounds as result of non-enzymatic browning, and such extracts do not meet the industrial needs of the cosmetic, pharmaceutical, food and nutraceutical markets. Although sugars can be used without necessarily being combined with amines, or vice versa, the biological material is capable of partnering with sugars on one hand, or amines on the other hand, facilitating initiation of the non-enzymatic browning reaction and thereby preventing the use of the extracts thus obtained for formulating consumer products. Furthermore, the constituents of the natural eutectic mixtures described in the patent family WO 2011/55829 may not always be suitable from the regulatory standpoint. This applies in particular to choline and its derivatives which are prohibited for use in cosmetics according to European Regulation N° 1223/2009. Added to the fact that in the case of eutectic mixtures formed from sugars, the microbial stability of the corresponding extracts is generally insufficient to envisage their incorporation into common consumer products stored for a sufficiently long period to permit the development of spoilage flora or pathogenic micro-organisms.

Furthermore, the eutectic mixtures are typically only formed for very precise proportions of defined constituents, which means that it is not sufficient to mix such and such a molecule, albeit natural, to obtain a lowering of the melting point of the mixture, and expect that mixture to be stable from the standpoint of crystallisation (by stability we understand at least one week). Also, these solvents present the drawback of being highly viscous at ambient temperature (generally above 100 cP). For example, the mixture of choline chloride and urea (molar ratio 1:2) has a viscosity of nearly 500 cP at 30° C. (Abbott, A. P., Capper, G., Davies, D. L., Rasheed, R. K., Tambyrajah, V., Novel solvents properties of choline chloride/urea mixtures, Chem. Commun., 2003, 7, 70-71), which is not without its problems in terms of extraction yields and renders it impossible to use industrially as an extraction solvent. In terms of molecular interactions, this high viscosity is attributed to the presence of a very dense network of hydrogen bonds between the constituents of the eutectic mixtures, thereby reducing the mobility of the free species present in these solvents. This viscosity is also attributable to the size of the ions (if present), from the low volume of space between the molecules, from electrostatic effects, and from Van der Waals interactions. All these factors combined constitute an impediment to the use of eutectic mixtures for the purpose of extracting plant (e.g. vegetable) substances, in so much as the shear forces necessary to place the extracting fluid in motion, and to make it penetrate into the biological material from which it is desired to extract all or part of the substances, will not be sufficient to permit optimum extraction. As a corollary, the low mobility of the chemical species in the eutectic mixture is problematic for dissolving the substances to be extracted, leading to low extraction yields, high energy costs, prolonged extraction times and/or large quantities of solvents.

Thus, it appears that there is currently no existing solution for extracting from a biological material ingredients or active principles such as phenolic compounds, antioxidants, saponins, carotenoids, terpenes or other, using fluid and low viscosity eutectic solvents based on betaine and in which the latter can also play a role of active ingredient or principle (by active ingredient we understand a substance having a technological action, while an active principle refers to any substance capable of exerting a cosmetic, pharmacological or nutritional action).

There is also a constant need for natural extraction solvent alternatives to substantiate and find potent activity for botanical extracts. This is because different solvents may differ in their extraction ability, resulting in a potential to derive various/different health benefits depending on the solvent used. Additionally, the use of novel extraction solvents, such as the eutectic solvents described herein, could allow for the discovery of novel activity and applications for botanicals.

The role of reactive oxygen species (ROS) in human diseases has been the subject of extensive studies relative to the prevention of diseases. Oxidative stress, caused by an imbalance between antioxidant systems and the production of oxidants, including ROS, seems to be associated with many multifactorial diseases, especially cancers, cardiovascular diseases, and inflammatory disorders. The mechanisms by which these diseases develop generally involve oxidative alteration of physiologically critical molecules, including proteins, lipids, carbohydrates, and nucleic acids, along with modulation of both gene expression and inflammatory response. Growing evidence suggests that, in addition to organism antioxidant defenses, intake of antioxidants may protect important biological molecules from oxidative damage and thus reduce the risk of numerous chronic diseases related to ROS.

Exposure to solar ultraviolet (UV) radiation is a causative factor in skin photodamage and carcinogenesis, and an urgent need exists for improved molecular photoprotective strategies different from (or synergistic with) photon absorption (Watson et al, 2014). Although the spatiotemporal consequences of UVR exposure for the composition and architecture of the dermal extracellular matrix (ECM) are well characterized, the pathogenesis of photoaging remains poorly defined. Several markers and pathways co-exist:

ROS are implicated in the aging processing

Extra-cellular matrix degradation

Loss of skin barrier function

And so on

Recent studies suggest a photoprotective role of cutaneous gene expression orchestrated by the transcription factor NRF2 (nuclear factor-E2-related factor 2) and the protein DJ-1. Indeed, the downregulation of DJ-1 impairs nuclear translocation of Nrf2 (Liu et al, 2014). The DJ-1/NRF2 pathway is clearly activated by cells to fight against oxidative stress-induced damage and this pathway acts as a protein cell marker of oxidative stress, highlighting the oxidative stress that is already present and affecting the cells. Active and botanical extracts may be able to interfer with this pathway, and therefore the use of active and botanical extracts may able to act prior to the activation of this pathway to. protect against oxidative stress-induced damage.

Thus, both topical antioxidants and inhibitors of detrimental cell signaling may be effective in abrogating the effects of specific UV-mediated protein degradation in the epidermis and dermis.

The listing or discussion of an apparently prior-published document in this specification should not necessarily be taken as an acknowledgement that the document is part of the state of the art or common general knowledge.

DISCLOSURE OF THE INVENTION

The present invention is based on the discovery of precise combinations comprising betaine or a hydrated form of betaine, and water, with at least one hydrogen bond donor among the organic acids and/or polyols, so as to obtain a synergy/improvement during the step of extracting compounds of industrial interest, preferably cosmetic, pharmaceutical or nutritional compounds and which may be heat sensitive, from a plant (e.g. vegetable) and/or animal and/or prokaryotic, and preferably plant (e.g. vegetable), biological material.

For the avoidance of doubt, as used herein, the skilled person would understand the term "plant" to mean a living organism of the kind exemplified by trees, shrubs, herbs, grasses, ferns, and mosses, typically growing in a permanent site, absorbing water and inorganic substances through its roots, and synthesizing nutrients in its leaves by photosynthesis using the green pigment chlorophyll. For example, the term plants may refer to flowers and vegetables (e.g. vegetables).

Among these compounds of interest we can mention in particular phenolic compounds including phenolic acids and esters, flavonoids, secoiridoids, stilbenes and phenolic alcohols, as well as antioxidants, carotenoids, alkaloids, lipids, phenylpropanoids, flavourings and taste modifiers, fragrances, biocides, antimicrobials, proteins, enzymes, colourings, pigments, surfactants and terpenoids including saponins.

More particularly compounds of interest include phenolic acids and esters, flavonoids, secoiridoids, phenolic alcohols, as well as antioxidants, carotenoids, alkaloids, lipids, phenylpropanoids, flavourings and taste modifiers, fragrances, biocides, antimicrobials, proteins, enzymes, colourings, pigments, and terpenoids including saponins.

In a first aspect, the invention provides a eutectic solvent for extracting plant (e.g. vegetable) and/or animal and/or prokaryotic biological material, wherein the solvent is a clear, stable and fluid mixture comprising:
(a) betaine or a hydrated form of betaine;
(b) at least one hydrogen bond donor compound selected from the group consisting of polyols and organic acids; and
(c) water
with the proviso that the eutectic extraction solvent does not comprise any exogenous sugar and/or amine salt and/or anion.

As used herein, the skilled person would understand that the term "clear" may mean that the solvent is transparent and contains no solid particles that are visible to the naked eye.

As used herein, the skilled person would understand that the term "stable" may mean that a solid phase, for example a crystal phase, does not form within the solvent within one week.

As used herein, the skilled person would understand that the term "fluid" may mean that the solvent exhibits flow. For example, may exhibit flow at a temperature of from about 10° C. to about 80° C., such as from about 20° C. to about 60° C., or from about 25° C. to about 45° C.

As used herein, the skilled person would understand that the term "exogenous" may mean that the specified compounds/components are not already present within the eutectic solvent, i.e. not contributed additionally.

As used herein, the skilled person would understand that the term "sugar" may mean any sugar compound as known to those skilled in the art, which may include sugars such as glucose, fructose and galactose.

As used herein, the skilled person would understand that the term "amine salt" may mean any positively charged amine specifies with a separate counter ion. For example, the term "amine salt" may refer to quaternary ammonium salts, such as choline.

As used herein, the skilled person would understand that the term "anion" may mean any negatively charged species. For example, the term "anion" may refer to $NO_3^-$, $F^-$, $Cl^-$, $Br^-$, $I^-$, $BF_4^-$, $ClO_4^-$, $CN^-$, $SO_3CF_3^-$ or $COOCF_3^-$.

In a particular embodiment, the invention provides a eutectic solvent for extracting plant (e.g. vegetable) and/or animal and/or prokaryotic biological material, wherein the solvent is a clear, stable and fluid mixture consisting essentially of:
(a) betaine or a hydrated form of betaine;
(b) at least one hydrogen bond donor compound selected from the group consisting of polyols and organic acids; and
(c) water.

As used herein, the skilled person would understand the term "consist essentially of", to mean that the eutectic solvents of the invention contain substantially no other components, particularly no further hydrogen bond donors known to be used in eutectic solvents.

In a further particular embodiment, the invention provides a eutectic solvent for extracting plant (e.g. vegetable) and/or animal and/or prokaryotic biological material, wherein the solvent is a clear, stable and fluid mixture consisting of:
(a) betaine or a hydrated form of betaine;
(b) at least one hydrogen bond donor compound selected from the group consisting of polyols and organic acids; and
(c) water.

In a further embodiment of the invention, the hydrogen bond donor compound may be selected from the polyols group consisting of: glycerol, erythritol, mannitol, sorbitol, ethylene glycol, propylene glycol, ribitol, aldonitol, propanediol, and pentylene glycol.

In a further embodiment of the invention, the hydrogen bond donor compound may be selected from the organic acids group consisting of: lactic acid, malic acid, maleic acid, pyruvic acid, fumaric acid, succinic acid, citric acid, acetic acid, aconitic acid, tartric acid, ascorbic acid, malonic acid, oxalic acid, glucuronic acid, neuraminic acid, sialic acid, shikimic acid, phytic acid, galacturonic acid, iduronic acid, hyaluronic acid, hydroxycitric acid, and lactone derivatives.

In an embodiment of the invention, the hydrogen bond donor is not citric acid.

In an embodiment of the invention, the critical molar ratio of betaine (or hydrated form of betaine) to the at least one hydrogen bond donor compound (polyols, or organic acids), is from 1:1.5 and 1:3, and is preferably 1:2.

In a further embodiment of the invention, the proportion by weight of water added to the mixture to obtain the solvent according to the invention is from 1 to 50%, and preferably 15 to 30% or 20 to 30%.

In an aspect of the invention, the eutectic extraction solvent may have a ratio of betaine or a hydrated form of betaine to the at least one hydrogen bond donor of from 1:1.5 to 1:3, such as 1:2; and a proportion of water added to the mixture of from 1 to 50%, and preferably 15 to 30% or 20 to 30%. For example, the solvent may have a ratio of betaine or a hydrated form of betaine to the at least one hydrogen bond donor of from 1:1.5 to 1:3; and a proportion of water added to the mixture of from 15 to 30%.

In a further aspect, the invention provides the use of an eutectic extraction solvent as previous defined for extracting natural biological compounds such as phenolic compounds including phenolic acids and esters, flavonoids, secoiridoids, stilbenes and phenolic alcohols, as well as antioxidants, carotenoids, alkaloids, lipids, phenylpropanoids, flavourings and taste modifiers, fragrances, biocides, antimicrobials, proteins, enzymes, colourings, pigments, surfactants and terpenoids including saponins, from plant (e.g. vegetable) and/or animal and/or prokaryotic biological material, and preferably from plant (e.g. vegetable) biological material.

In an further embodiment, the invention provides the use of an eutectic extraction solvent as previous defined for extracting natural biological compounds such as phenolic compounds including phenolic acids and esters, flavonoids, secoiridosides, phenolic alcohols, as well as antioxidants, carotenoids, alkaloids, lipids, phenylpropanoids, flavourings and taste modifiers, fragrances, biocides, antimicrobials, proteins, enzymes, colourings, pigments, and terpenoids including saponins, from plant (e.g. vegetable) and/or animal and/or prokaryotic biological material, and preferably from plant (e.g. vegetable) biological material.

In an embodiment of the use of the invention, the plant (e.g. vegetable) biological material may be selected from the group consisting of cherry blossom, horsetail, plantain, saffron flowers, chrismum, rose of Jerico, rosemary, Selaginella pulvinata, Tillandsia usnoides and olive leaves.

In a further embodiment of the use of the invention, the plant (e.g. vegetable) biological material may be selected from the group consisting of cherry blossom, horsetail, plantain, saffron flowers, chrismum, rose of Jerico, rosemary, and olive leaves.

Without wishing to be bound by theory, it appears that the synergy/improvement obtained with the solvent according to the invention derives from a natural physico-chemical phenomenon that will be refered to hereafter as "eutectigenesis" and which corresponds to the formation of a eutectic mixture produced when the critical proportions of the mixture corresponding to the eutectic point are reached. The eutectic point is the point on the phase diagram at the intersection of the two liquidus curves, giving the composition at which the mixture is at its minimum temperature in liquid phase.

In a totally unexpected manner, it has been found that the combination of three compounds—(a) betaine (or hydrated form of betaine), (b) hydrogen bond donor and (c) water—in well defined proportions, such as from 1:1.5 to 1:3 or 1:2, makes it possible to extract natural substances in a synergistic/improved fashion. The absence of one of (a) to (c) leads to a collapse of the recovery rate. This discovery is all the more significant in that until now there did not exist any known theoretical model, empirical rule, or mechanism of action by which to infer or predict any extraction synergy for eutectic mixtures based on betaine. At most, mention is made in the family of documents WO 2011/55829 to the effect that deep eutectic solvents are often formed from two compounds present in an equimolar ratio (1:1).

The present inventors have surprisingly and unexpectedly shown that this critical point is systematically reached for a molar ratio of betaine (or hydrated form of betaine):hydrogen bond donor of from 1:1.5 to 1:3, and preferably 1:2. Thus, the critical point on the phase diagram corresponds to the critical composition of the extracting mixture for which the extraction efficiency for natural substances is optimal, which it appears no prior work has hitherto been able to demonstrate.

In addition, the mechanism of formation of eutectic mixtures described by Abbott et al. (patent family U.S. Pat. No. 7,183,433; Abbott, A. P., Capper, G., Davies, D. L., Rasheed, R. K., Tambyrajah, V., Novel solvents properties of choline chloride/urea mixtures, Chem. Commun., 2003, 7, 70-71) postulates that lowering of the melting point is the consequence of the establishment of a hydrogen bond between a hydrogen bond donor and the anion (negatively charged ion) of an amine salt. It is therefore surprising to find in the results presented below that a lowering of the melting point is obtained when no anion is contributed exogenously. This represents an advance in terms of scientific knowledge which takes advantage of the amphoteric character of betaine. Whereas many authors are overly focused on amine salts, particularly in the eutectic mixtures and ionic liquids described in the patent family document U.S. Pat. No. 7,183,433, the natural eutectic mixtures covered by the present invention systematically include an amine without anions (contributed exogenously) as the latter are not necessary for the mechanism of eutectigenesis.

In terms of the extraction composition, the invention discloses the addition of a proportion by weight of exogenous water (i.e. contributed and not already present in the mixture of betaine and hydrogen bond donor) comprised between 1 and 50%, preferably between 15 and 30% or 20 to 30% in the binary mixtures betaine:glycerol and betaine:lactic acid, which have a critical molar ratio of betaine:hydrogren bond donor from 1:1.5 to 1:3, and preferably 1:2, so as to lower the viscosity to a threshold that is both compatible with an industrial use and with the designation of eutectic mixture. Specifically, it is known to the person skilled in the art that the hydrogen bonds that enable the formation of supramolecular complexes characteristic of eutectic solvents are broken for proportions of water by volume greater than 50% (Gutierrez M. C., Ferrer, M. L., Mateo, C. R., del Monte, F. Freeze-drying of aqueous solutions of deep eutectic solvents: a suitable approach to deep eutectic suspensions of self-assembled structures, Langmuir, 2009, 25, 5509-5515).

The described extraction method of the present invention with ternary mixtures containing water, betaine and a hydrogen bond donor among polyols and organic acids as defined herein retains the critical eutectigenesis molar ratio of from 1:1.5 to 1:3, and preferably 1:2, between betaine and the hydrogen bond donor; a ratio that is generic for binary mixtures (betaine:hydrogen bond donor) and for ternary mixtures (water:betaine:hydrogen bond donor) and provides a spectacular improvement in the actives contained within extract obtained using the extraction method of the invention. Thus, the method enables the yield of the actives to be multiplied by up to 45 times and improves the richness of the chromatographic profiles to be obtained by virtue of different eutectic mixtures that are liquid at ambient temperature, such as from about 10° C. to about 80° C., such as from about 20° C. to about 60° C., or from about 25° C. to about 45° C., and based on agro- and/or bio-sourced natural compounds available in industrial quantities such as betaine, polyols (such as glycerol) and organic acids (such as lactic acid) as by-products of sugar production, oil chemistry and biotechnology.

The extraction method of the present invention consists of maceration, percolation and/or infusion of a ground or unground biological material immersed in a eutectic solvent, at between 20 and 60° C., such as from about 25° C. to about 45° C., at atmospheric pressure or under pressure, for example at a pressure of from about 100 to about 500 kPa, with stirring for 1 to 5 hours, preferably for 2 hours. The extraction phase does not involve any chemical transformation between any of the compounds present in the eutectic extraction solvent which remain totally inert vis-à-vis the biological material and the natural substances to be extracted. For example, none of the compounds present in the eutectic extraction solvent react with the biological material and the natural substances to be extracted in a covalent manner; at the extraction temperatures described in this invention (<60° C.), only non-covalent interactions between the natural substances take place.

As used herein, the skilled person would understand that the term "ground" may mean that the biological material had been subjected to mechanical forces to crush, pulverize, or reduce to powder by friction prior to being macerated, percolated and/or infused in the eutectic exctraction solvent.

As used herein, the skilled person would understand that the term "unground" may mean that the biological material had not been subjected to any mechanical forces prior to being macerated, percolated and/or infused in the eutectic exctraction solvent.

The extraction method of the present invention by eutectigenesis described here was specifically developed to obtain an optimum microbial stability without the addition of exogenous preservatives either to the extracting fluid or the liquid extracts. The said extracts, obtained following maceration, percolation and/or infusion of the biological material in the eutectic solvents, and on completion of the filtration and conditioning operations, for example filtering through a bag and/or plate filter, were found to be stable from the microbiological standpoint, i.e. the extract obtained did not comprise a microbiological load that would be considered to be hazardous and/or toxic to human health despite the microbial load of the biological material input at the initial extraction step. Thus, the eutectic mixtures and extracts obtained are free of preservative agents that are known by the person skilled in the art to be capable, in certain confirmed cases, of exerting a toxic effect in humans, particularly in terms of endocrine disruptors. The good microbial stability of these solvents provides a means of indirectly improving their safety, particularly in view of the fact that it would appear contradictory to use a non-toxic eutectic solvent only to then proceed to add potentially toxic antimicrobials.

In a further aspect, the present invention provides a method for extracting natural biological compounds according to the invention comprising the following steps:

a. immersing, while stirring, a ground or unground biological material in the extraction solvent according to the invention, then b. macerating or percolating or infusing the mixture obtained in step a. at a temperature between 20 and 60° C., then c. filtering the extraction product obtained at b., thereby obtaining a natural biological liquid extract derived from the plant (e.g. vegetable) and/or animal and/or prokaryotic biological material.

The extraction product obtained in b. may be filtered in step c. using any techniques known to those skilled in the art.

Thus, in a further aspect, the invention also provides a natural biological liquid extract comprising plant (e.g. vegetable) and/or animal and/or prokaryotic biological material obtained or obtainable by the extraction method or use previously defined.

The natural biological liquid extract may be further purified before being used or the extract may be used without any further purification. Examples of purification that may be used include, but are not limited to, chromatography, distillation, and/or evaporation.

In a particular aspect, the present invention provides a natural biological extract and a eutectic solvent as defined herein. Typically, the eutectic solvent may be present in an amount of from about 0.01 to about 50% by weight, or from about 0.1 to about 25% by weight.

When the natural biological liquid extract is obtained by the method of the invention, the filtering step c. may remove all of the eutectic solvent present. Alternatively, the filtering step may leave residual solvent present within the extraction product.

Accordingly, in a further embodiment, the invention also provides a natural biological liquid extract comprising a eutectic solvent according to the present invention. Typically, the eutectic solvent may be present in an amount of from about 0.01 to about 50% by weight, or from about 0.1 to about 25% by weight.

The natural biological compounds that may be extracted by the method of the invention may include phenolic acids and esters, flavonoids, secoiridoids, stilbenes and phenolic alcohols, as well as antioxidants, carotenoids, alkaloids, lipids, phenylpropanoids, flavourings and taste modifiers, fragrances, biocides, antimicrobials, proteins, enzymes, colourings, pigments, surfactants and terpenoids including saponins, from plant and/or animal and/or prokaryotic biological material.

For example, natural biological compounds that may be extracted by the method of the may invention include phenolic acids and esters, flavonoids, secoiridoids, phenolic alcohols, as well as antioxidants, carotenoids, alkaloids, lipids, phenylpropanoids, flavourings and taste modifiers, fragrances, biocides, antimicrobials, proteins, enzymes, colourings, pigments, terpenoids including saponins, from plant and/or animal and/or prokaryotic biological material.

In an embodiment of the method of the invention, the plant biological material may be selected from the group consisting of cherry blossom, horsetail, plantain, saffron flowers, chrismum, rose of Jerico, rosemary, Selaginella pulvinata, Tillandsia usnoides and olive leaves.

For example, the plant biological material may be selected from the group consisting of cherry blossom, horsetail, plantain, saffron flowers, chrismum, rose of Jerico, rosemary, and olive leaves.

In a further aspect, the present invention provides a natural biological liquid extract characterised in that the plant (e.g. vegetable) biological material from which it is derived may be selected from the group consisting of cherry blossom, horsetail, plantain, saffron flowers, chrismum, rose of Jerico, rosemary, Selaginella pulvinata, Tillandsia usnoides and olive leaves. For example, the plant (e.g. vegetable) biological material may be selected from saffron flower, chrismum or rose of Jericho.

The extraction method according to the invention is particularly remarkable in that it exerts a synergistic/improved action on the process of extracting the biological material. In addition, the natural biological liquid extract obtained by putting into effect the said extraction method reinforces the biological and/or physico-chemical activity of the compounds included in said extract. For example, the results obtained with cherry blossom clearly show the superiority of the extracts obtaining using the eutectic mixtures studied (compared with more conventional solvents such as hydroglycerin mixtures which are widely used in the cosmetics and aromatics industry) over a wide range of biological activity such as photo-protection, collagen synthesis, anti-inflammatory action (TNFα pathway), or inhibition of the release of type 1 matrix metalloproteinases (MMP-1) following UV stimulation (protection against photo-ageing).

The results obtained with saffron flowers, chrismum and rose of Jericho demonstrate the strong inhibition on melanin synthesis (hypo-pigmenting effect) exerted by eutectic extracts of saffron flowers, chrismum and rose of Jericho (around 55, 33 and 36%, respectively) compared with their hydroglycerin homologues that are devoid of any activity. Moreover, TNFα inhibition (anti-inflammatory response)

for eutectic extracts of horsetail and the antioxidant activities thereof are far superior to those of hydroglycerin extracts of the same plant. This also applies to rosemary, the extraction of which using eutectic solvents based on betaine induces an antioxidant activity higher by a factor of 2 than extracts derived form a process employing a water:glycerol mixture by weight (1:1). Furthermore, the examples show that collagen synthesis on a fibroblast model and photo-protection are better with eutectic extracts of olive leaves compared with hydroglycerin extracts of olive leaves.

The present inventors have surprisingly and unexpectedly found that these biological and/or physico-chemical activities that are strengthened by the use of eutectic solvents for extractive purposes were relatively well correlated to the corresponding chromatographic profiles. Specifically, the profiles obtained by eutectic extraction are generally "unattainable" by more conventional solvents. The profiles differ not only in quantitative terms, that is the specific amount of a certain molecule within the extract, but even more significantly in qualitative terms. For example, while most of the molecules normally extractable by conventional solvents are present in the eutectic extracts, the latter, however, contain new active substances that are absent from hydroglycerin extracts. For example, caffeoyl glucoside, chlorogenic acid and dicaffeoylquinic acid have been identified for the first time in cherry blossom due to the use of eutectic solvents, as well as the kaempferol-3-O-lactyl-sophoroside isomers in saffron flower. The discovery of these new phyto-actives highlight the improved properties (whether it be biological or physico-chemical properties) of eutectic extracts, and opens up new avenues for the utilisation of extracts exhibiting novel activities. For example, dicaffeoylquinic acid discovered in the eutectic extracts of cherry blossom is a selective and highly effective inhibitor of type 1 human immunodeficiency virus (HIV-1) involved in the aetiology of acquired immunodeficiency syndrome or AIDS (Robinson et al., Dicaffeoylquinic acid inhibitors of human immunodeficiency virus integrase: inhibition of the core catalytic domain of human immunodeficiency virus integrase, Mol. Pharmacol. 1996, 50, 846-855).

In a further aspect, the present invention provides the use of a natural biological liquid extract as defined herein for the manufacture of a nutraceutical composition, a dietary or a food product for humand or animal, a nutritional supplement, a fragrance, a pharmaceutical, oenological or cosmetic formulation, intended to be administered orally, parenterally, or for topical, rectal, nasal, auricular, vaginal and/or ocular application.

In a further aspect, the present invention provides the use of said the natural biological liquid extract for the manufacture of a nutraceutical composition, a dietary or food product for humans or animals, a nutritional supplement, a fragrance or flavouring, a pharmaceutical, oenological or cosmetic formulation or composition.

For example, the present invention provides the use of said the natural biological liquid extract for the manufacture of a nutraceutical composition, a dietary or food product, a nutritional supplement, a pharmaceutical composition, or cosmetic formulation or composition.

In a further embodiment, the invention also provides the use of a liquid extract in a nutraceutical composition, a dietary or food product for humans or animals, a nutritional supplement, a fragrance or flavouring, oenological or cosmetic formulation.

In a further embodiment, the invention provides a pharmaceutical composition comprising a natural biological liquid extract as defined herein.

In a further embodiment, the invention provides a liquid extract as defined for use in a pharmaceutical composition, and further provides a liquid extract or pharmaceutical composition for use as photo-protective, anti-photo-ageing, hypo-pigmenting, bleaching, anti-ageing, anti-oxidant, anti-radical, reducers of oxygen reactive species, reducers of advanced glycation end-products, metalloproteinase inhibitors, anti-inflammatories, skin soothing agents, collagen synthesis activators, hydrating agents, restorers of barrier function for the skin or improvers of cell adhesion and cohesion.

For example, the liquid extract or the pharmaceutical composition may be used as photo-protective, anti-photo-ageing, hypo-pigmenting, bleaching, anti-ageing, anti-oxidant, anti-radical, reducers of oxygen reactive species, metalloproteinase inhibitors, anti-inflammatories, skin soothing agents, collagen synthesis activators, hydrating agents, or restorers of barrier function for the skin.

Typically, in an embodiment of the invention, the compositions or formulations of the invention are intended to be administered orally or parenterally, or for topical, rectal, nasal, auricular, vaginal and/or ocular application.

In a further aspect, the present invention provides a natural biological liquid extract derived from cherry blossom as a photo-protective, barrier function protector, anti-oxidant and anti-photo-ageing agent. For example, the natural biological liquid extract derived from cherry blossom may act as a photo-protective, and anti-photo-ageing agent.

In a further embodiment, the present invention provides a natural biological liquid extract derived from the group consisting of cherry blossom, horsetail, plantain, saffron flowers, chrismum, rose of Jerico, rosemary, Selaginella pulvinata, Tillandsia usnoides and olive leaves as a photo-protective, barrier function protector, anti-oxidant and anti-photo-ageing agent.

The data presented herein show that the formulation of eutectic liquid extracts in water, for example, make it possible obtain a high level of biological and/or physico-chemical activity between 0.001 and 10%, preferably between 0.01 and 1% (v). A certain number of eutectic extracts claimed in the present invention exert a higher activity than that of their hydroglycerin homologues, even when the latter are ten times more concentrated in the final liquid formulation.

Other compositions of extracting fluids shown in Table 4 were tested, which generally led to the formation of a mixture that crystallises at ambient temperature, and when cold or hot, thereby rendering any extraction from any biological material impossible. Furthermore, tests with citric acid also show the difficulty of obtaining stable extracting eutectic mixtures from betaine. Table 3 shows the influence of the composition of the binary mixture betaine:citric acid on the macroscopic appearance of the medium. While a molar ratio of 50:50 or 40:60 makes it possible to delay the formation of a crystalline phase after one week compared with the ratio 20:80, we note however that these conditions are not conducive to an industrial development.

It can also be seen herein in Example 4 that a large number of eutectic mixtures generally presented as potentially interesting from the industrial standpoint, and often including sugars but not only sugars, turn yellow, orange or brown at 50° C., and polymerise, become cloudy or crystallise (Table 4). A small number of mixtures remain liquid and clear for more than a month at 4° C., ambient temperature and 50° C.; the ternary mixtures betaine:glycerol:water (2:3, molar plus 25% by weight of water) and betaine:lactic acid:water (2:3, molar plus 25% by weight of water) form part of fluids which, in themselves, have no impact on the colour of formulations intended for cosmetic, pharmaceutical or food use. In other words, there will be no addition of any colour load intrinsic to the extracting fluid to the colouring already imparted by the extraction of colouring substances from a biological material.

In a further aspect, the present invention provides a natural biological liquid extract as defined, characterised in that it reinforces the biological and/or physio-chemical activity of the compounds included in said extract.

Ultimately, the liquid extracts obtained by application of the extraction method by eutectigenesis claimed in the present invention have an increased content of compounds of interest compared with more conventional solvents like water or hydro-glycerin mixtures commonly used in the cosmetics, nutraceuticals and pharmaceuticals industry. What is more, the eutectic solvents and methods of the present invention can also perform as well as, or even better than, state-of-the-art intensified extraction technologies using subcritical water for example.

Eutectic extracts obtained from a large number of biological materials have a potential application as photoprotective, anti-photo-ageing, hypo-pigmenting, bleaching, anti-ageing, antioxidant and antiradical agents, reducers of oxygen reactive species, reducers of advanced glycation end-products, metalloproteinase inhibitors, anti-inflammatories, skin soothing agents, collagen synthesis activators, hydrating agents, restorers of the barrier function of the skin or improvers of cell adhesion and cohesion.

For example, the extracts obtained may be used as photoprotective, anti-photo-ageing, hypo-pigmenting, bleaching, anti-ageing, antioxidant and antiradical agents, reducers of oxygen reactive species, metalloproteinase inhibitors, anti-inflammatories, skin soothing agents, collagen synthesis activators, hydrating agents or restorers of the barrier function of the skin.

By virtue of the extraction capacity of said eutectic solvents, new biological properties can emerge from the extracted biological materials. For example, it has been found by the present inventors that the activity discovered for the eutectic extract of cherry blossom may have protective properties in terms of photo-ageing and could be used as a cosmetic, nutraceutical and/or food agent. It is known to the person skilled in the art that light radiation in the range of wavelengths comprised between 280 and 400 nm is known to induce browning of the human epidermis. Radiation in the range comprised between 280 and 320 nm (UV-B) causes erythema and burning of the skin adversely affecting natural tanning. UV-A rays between 320 and 400 nm cause deterioration of the skin manifesting as a loss of elasticity and the appearance of premature ageing, in particular via the breakdown of the extra-cellular matrix. There is therefore a high demand for means of controlling these unpleasant effects for aesthetic and health reasons. The cherry blossom extract described in the present invention is capable of acting (i) as an agent for controlling the inflammatory reaction induced by UV radiation, (ii) as an inhibitor of the breakdown of the extra-cellular matrix following UV exposure, and (iii) as a protector of the cellular viability of cells exposed to UV.

Furthermore, as the eutectic solvents are edible and non-toxic, the corresponding extract can be directly formulated in foodstuffs and beverages (for humans and animals), as well as in cosmetic, nutraceutical, cosmeceutical, oenological, aromatic (fragrances and flavourings) and pharmaceutical products in proportions of incorporation in the finished product ranging from 0.001 to 20% or 0.01 to 20%, preferably from 0.01 to 10% or 0.1 to 10% and ideally from 0.05 to 5% or 1 to 5%. Liquid extracts enriched with compounds of interest in solution in a eutectic mixture can also be consumed directly via the oral or parenteral route, or by topical, rectal, nasal, auricular, vaginal and/or ocular application.

The skilled person will understand that all references herein to particular aspects of the invention include references to all embodiments and combinations of one or more embodiments of that aspect of the invention. Thus, all embodiments of particular aspects of the inventions may be combined with one or more other embodiments of that aspect of the invention to form further embodiments without departing from the teaching of the invention.

Experimental Methods

1. Preparation of Eutectic Solvents

The different constituents of the eutectic mixtures (glycerol, lactic acid, citric acid and betaine) are weighed in an Erlenmeyer flask in no particular order. Tap water, but preferably demineralised or distilled water, is then added at a concentration by weight that will preserve the physico-chemical and microbial integrity, between 1 and 50%, preferably between 15 and 35%, and ideally accounting for 25% by weight of the mixture. The eutectic mixtures chosen in this document are betaine:citric acid (2:3, mol), betaine:glycerol (2:3, mol) and betaine:lactic acid (2:3, mol), each containing 25% by weight of water, although it is to be appreciated that other combination of betaine and hydrogen bond donor as defined could be used. The mixture is heated to 50° C.+/−2° C. and homogenised under magnetic stirring. Once the medium is fully dissolved and melted, it is placed at ambient temperature then stored in a container until use.

2. Solid/Liquid Extraction by Maceration at 50° C.

The various pre-dried plant (e.g. vegetable) matrices are ground (IKA manual grinder), with the exception of rosemary, then immersed in a conventional solvent (water, water/glycerol, water/lactic acid, water/citric acid) or eutectic solvent (see the Examples). A ratio of 5% of plant (e.g. vegetable) matrix (20 M) was applied for all of the extractions. The mixture is heated at 50° C. for 2 h under magnetic stirring in a 100 ml glass beaker. One pass is performed, after which the medium is hot filtered through a 25 μm bag filter or plate filter then again through a 5-7 μm plate filter.

3. Intensification of Extraction by Subcritical Water

The pre-dried plant (e.g. vegetable) matrix is ground (IKA manual grinder) then immersed in water in a 150 mL glass reaction vessel. A ratio of 5% of plant (e.g. vegetable) matrix (20 M) was applied for the extractions. To homogenise the temperature, the reactor is surrounded with distilled water (700 mL) and placed in a microwave cavity. The extraction is performed by means of a high performance microwave reactor (1.2 kW, UltraClave, Milestone, Italy). Before starting the extraction, the oxygen is removed by placing the vessel under vacuum, then the reactor space and extraction medium are saturated in nitrogen at an initial pressure of 30 bars. The setpoint pressure and temperature are reached by virtue of the nitrogen flow and microwave heating, respectively. The extraction temperature is set at 125° C. and the initial pressure at 30 bars. These two parameters are controlled by external sensors. When the temperature reaches the setpoint value of 125° C. (within 15 minutes in our experience) extraction is performed for 30 minutes in a single pass. Once the extraction is complete, the medium is hot filtered through a 25 μm bag filter or plate filter then again through a 5-7 μm plate filter.

4. Quantification of Compounds of Interest by High Performance Liquid Chromatography (HPLC)

The liquid extracts thus obtained are analysed directly by HPLC without preliminary concentration or drying.

4.1. Proportion of Rosmarinic Acid in the Liquid Extracts of Rosemary

Quantification and identification of rosmarinic acid are performed using an analytical standard (Extrasynthese—reference: 4957S) and by plotting a calibration curve. The Agilent 1100 HPLC apparatus is equipped with a UV-Visible DAD detector or equivalent. An elution gradient is used via a mixture of HPLC grade acetonitrile and HPLC grade water with an addition of 99% trifluoroacetic acid (TFA). The following chromatography conditions are used:

Zorbax Eclipse XDB C18 column, 1.8 µm, 4.6 mm×50 mm or equivalent.

Mobile phase:

| Time (min) | % acetonitrile 0.1% TFA | % water 0.1% TFA |
|---|---|---|
| 0 | 15 | 85 |
| 2 | 15 | 85 |
| 2.5 | 18 | 82 |
| 2.7 | 100 | 0 |
| 3.5 | 100 | 0 |

Flowrate: 2 mL/minute
Detection: 328 nm
Temperature: 60° C.
Injection volume: 2 µL
Pressure: 210 bars±5 bars
The following retention times are observed:

| Compound | Retention time (minutes) |
|---|---|
| Rosmarinic acid | 2.0 |
| Luteolin 3-glucuronide | 2.3 |

4.2. Proportion of Oleuropein in the Liquid Extracts of Olive Leaves:

Quantification and identification of oleuropein are performed using an analytical standard (Extrasynthèse—reference: 0204) and by plotting a calibration curve. The Agilent 1100 HPLC apparatus is equipped with a UV-Visible DAD detector or equivalent. An elution gradient is used via a mixture of HPLC grade acetonitrile and HPLC grade water with an addition of 99% trifluoroacetic acid (TFA). The following chromatography conditions are used:

Zorbax Eclipse XDB C18 column, 1.8 µm, 4.6 mm×50 mm or equivalent.

Mobile phase:

| Time (min) | % acetonitrile + 0.1% TFA | % water + 0.1% TFA |
|---|---|---|
| 0 | 20 | 80 |
| 2.6 | 20 | 80 |
| 2.7 | 100 | 0 |
| 3.5 | 100 | 0 |

Flowrate: 1.5 mL/minute
Detection: 230 nm
Temperature: 40° C.
Injection volume: 2 µL
Pressure: 210 bars±5 bars The following retention times are observed:

| Compound | Retention time (minutes) |
|---|---|
| Oleuropein | 2.6 |

5. Chemical Characterisation of Liquid Extracts by High-Performance Liquid Chromatography The chromatographic conditions hereinbelow were applied with a view to identifying and quantifying the compounds present in the various extracts produced.

Analytical column: Atlantis T3 150×4.6 mm C18-5 µm or equivalent
Temperature: 30° C.
Flowrate: 0.6 mL/min
Pressure: 60-100 bars
Detection: depending on the compounds to be quantified—350 or 280 nm.
Injection volume: 7 µl
Mobile phase:
A: Acetonitrile:$H_2O$ (450/50 v:v)+0.1% acetic acid
B: $H_2O$+0.1% acetic acid

| Time (min) | Solvent A (%) | Solvent B (%) |
|---|---|---|
| 5 | 5 | 95 |
| 15 | 5 | 95 |
| 20 | 70 | 30 |
| 30 | 80 | 20 |

6. Stability Test

After obtaining the eutectic mixtures, their behaviour over time is monitored at three different temperatures (4° C., ambient temperature, 50° C.) in order to assess their impact in a formulation for example for cosmetic use. Specifically, in an industrial context, an extract must be capable of retaining its colour integrity during an industrial process and during use by consumers.

7. Test of Physico-Chemical Efficacy as Antioxidant

The capacity of the extracts to trap peroxyradicals is determined using the reference method published by Ou et al. Determination of total antioxidant capacity by oxygen radical absorbance capacity (ORAC) using fluorescein as the fluorescent probe: First action 2012.23. Journal of AOAC International, 2013, 96, 1372-1376) in the AOAC Official Journal. For information, the AOAC is the Association of Official Agricultural Chemists of the United States Department of Agriculture (USDA). All phosphate buffer solutions (pH 7.2) containing the desired concentrations of antioxidants (from 0 to 40 µM) are prepared extemporaneously. Fifty millilitres of each solution are transferred by multi-channel pipette into a Fluotrac 96-well microplate (Greiner). Each well is then topped up with 100 µL of phosphate buffer solution, pH 7.2, containing 0.126 µM of fluorescein disodiium salt. To improve the repeatability, the microplate is pre-heated at 37° C. under orbital stirring at 1200 rpm in a temperature-controlled thermoshaker (PHMT series, Grant Instruments Ltd, Shepreth, England) for 20 minutes. 50 µL of AAPH solution in freshly prepared phosphate buffer solution are then added using a multi-channel pipette. Ultimately, each well contains 200 µL of final mixture composed of 0.063 M of fluorescein disodiium salt, 12.7 mM of AAPH and increasing concentrations of antioxidants (from 0 to 10 µM) in phosphate buffer solution. A drop in fluorescence to 515 nm (λex: 490 nm) is immediately recorded. Measurements are taken every minute for 2 hours at 37±0.1° C. with 5 seconds of stirring before each measurement using a microplate reader. The results are then calculated according to Ou et al. Development and validation of an improved oxygen radical absorbance capacity using fluorescein as the fluorescent probe. J. Agric. Food Chem. 2001, 49, 4619-4626) in µmol of Trolox equivalent per g of liquid extract (ORAC value).

8. Biological Efficacy Tests

All efficacy tests were performed for non-cytotoxic concentrations according to each cellular type used.

8.1. Anti-Inflammatory Activity (Inhibition of TNFα)

The in vitro test of anti-inflammatory activity is based on the strong inflammatory response that keratinocytes are capable of inducing after sun exposure. The HaCaT cells (human immortalized keratinocytes, Life-technology, N° P612451, Batch 09543), with a passage number below 50, were used. The cells were cultured in the following cell medium: DMEM with L-glutamine (Dulbecco's Minimum Essential Medium, PAN BIOTECH. Batch 97487) supplemented with penicillin (100 IU/mL) and streptomycin (100 µg/mL; PAN BIOTECH, Batch 20145241), and with 10% inactivated foetal calf serum (PAN BIOTECH, Batch P440011), pH 7.2.

A negative control using a saline solution (HESS, SIGMA) and a positive control using dexamethasone at 10 µM, were set up.

$1.10^5$ cells/mL (500 µL/well) were placed in culture in 48-well culture plates and incubated at 37° C. (5% $CO_2$) for 24 h. At the end of this incubation period, the cells were placed in culture with a serum-free medium containing the extracts to be tested for 1 hour preceding UV stimulation. Irradiation was performed using a Suntest CPS+ simulator (Atlas Material Testing Technology BV, Moussy le Neuf, France) equipped with a xenon lamp (1100 W). The irradiance was set at 750 $W/m^2$ with a combined light dose in the order of 15 $mJ/cm^2$ for 1 minute. The cells were then re-cultured for 24 hours.

At the end of this incubation period, the supernatant was recovered from the culture in order to measure the TNF-alpha released by the cells. The ELISA RAB068 Human TNF-alpha kit (SIGMA-ALDRICH) was used for this purpose. The optical densities (OD) of each well were then measured at 450 nm using an Infinite M200 Pro microplate reader (TECAN). The results obtained were then compared with the untreated well in order to express the protection gain in relation to the positive control (in %):

Protection gain =

$$100 - 100 * \frac{(\text{Mean } OD \text{ test well} - \text{Mean } OD \text{ negative control})}{\text{Mean } OD \text{ positive control} - \text{Mean } OD \text{ negative control}}$$

8.2. Melanogenesis Inhibiting Activity (Hypo-Pigmenting Effect)

The biological model set up for this test was the NHEM-LP cell type (for human melanocyte, slightly pigmented). These cells were placed in culture at 37° C. and 5% $CO_2$ in a medium of M254 supplemented with HMGS-2 (without PMA), insulin (5 µg/mL), penicillin (50 µg/mL), streptomycin (50 µg/mL) and gentamycin (25 µg/mL).

In the first instance, non-cytotoxic concentrations of the eutectic extracts under test were evaluated. For this purpose, different incubation times were tested. On completion of these successive stimulations, the NHEM-LP cells were incubated with MTT (tetrazolium salt), which is reduced to blue formazan crystals by the mitochondrial enzyme succinate dehydrogenase. The optical density after dissolutions of the formazan crystals by DMSO was measured using a micro-plate reader (VERSAmax, Molecular Devices).

The melanocytes were placed in culture in 24-well plates for 24 hours. The medium was changed after 24 h and replaced by medium that had been (or had not been) pre-stimulated. The positive control consisted of a stimulation of the cells by lipoic acid (5 µg/mL) in the presence of L-tyrosine (1 mM). A control (non-stimulated well) was also present on the plate. The cells were then incubated for 10 days with a two fresh treatments after 3 and 7 days of incubation. At the end of the incubation the supernatants were recovered and melanin synthesis was quantified on the cell layers. For this purpose the melanin was extracted by cellular lysis using an NaOH solution at 0.5 N. The optical density was then measured at 405 nm. The quantification was carried out using a calibration curve pre-validated according to a standard (standard curve from 0.39 to 100 µg/mL).

The percentage inhibition was calculated by the following formula:

$$\text{Inhibition (\%)} = \frac{\text{Mean of stumulated control} - \text{Test condition}}{\text{Mean of stimulated control} - \text{Mean of non-stimulated control}} \times 100$$

8.3. Photo-Protective Effects

The in vitro test to evaluate the photo-protective effect was used to identify compounds or extracts having photo-protective properties in terms of the cellular viability of cells exposed to a cytotoxic dose of solar radiation.

Two protocols were used:
Pre-treatment of cells with the extract under test before exposure to solar radiation,
Post-treatment of cells with the extract after exposure to solar radiation.

Cytotoxicity was measured 24 hours after exposure using neutral red which is a weak cationic dye that penetrates the cell membranes and accumulates in the intracellular lysosomes. This in vitro test was conducted on a cell line of HaCaT keratinocytes (human immortalized keratinocytes, Life-technology, N° P6110401, Batch 091006) with a passage number below 50. The cells were cultured in the following medium: DMEM with L-glutamine (Dulbecco's Minimum Essential Medium, PAN BIOTECH. Batch 5530513) supplemented with penicillin (100 IU/mL) and streptomycin (100 µg/mL; PAN BIOTECH, Batch 9230112), and with 10% inactivated foetal calf serum, (PAN BIOTECH, Batch P290907), pH 7.2.

A negative control using a saline solution (HBSS, SIGMA) and a positive control using Trolox (SIGMA) at concentrations of 10, 20 and 50 µg/ml, were set up.

$1.10^5$ cells/mL (500 µL/well) were placed in culture in 48-well culture plates and incubated at 37° C. (5% $CO_2$) for 24 h. In the pre-treatment protocol, the culture medium was replaced by 100 µL of saline solution containing the extract at different concentrations, in contact with the cells for 1 h at 37° C. (5% $CO_2$). At the end of this incubation period, the stimulation was withdrawn to be replaced by 100 µL of HBSS. Irradiation was then performed using a Suntest CPS+ simulator (Atlas Material Testing Technology BV, Moussy le Neuf, France) equipped with a xenon lamp (1100 W). The irradiance was set at 750 $W/m^2$ with a combined light dose in the order of 20 $mJ/cm^2$ for 4 minutes. The cells were then replaced in culture for 18-22 hours in the customary culture medium. In the post-treatment protocol, the culture medium is replaced by 100 μL of HBSS saline solution. Irradiation was then performed using a Suntest CPS+ simulator (Atlas Material Testing Technology BV, Moussy le Neuf, France) equipped with a xenon lamp (1100 W). The irradiance was set at 750 W/m² with a combined light dose in the order of 20 mJ/cm² for 4 minutes. The cells were then stimulated using extracts with different non-cytotoxic concentrations and replaced in culture for 18-22 hours in the customary culture medium.

In both protocols, after 18-22 hours of incubation, the cells were washed then placed in a medium containing 50 μg/mL of neutral red and incubated at 37° C. and 5% $CO_2$ for 3 hours. The medium was then removed to wash the cells and eliminate the excess neutral red. A decolouring solution (50% ethanol, 1% acetic acid, 49% distilled water; 50 μl per well) was added to the cells. The 48-well plates were then agitated for 15-20 minutes at ambient temperature away from light. The degree of cell membrane damage (increase in the release of red neutral) was measured at 540 nm using an Infinite M200 Pro microplate reader (TECAN). The optical densities (OD) of each well were then measured. The results obtained were then compared with the untreated well (HBSS, 100% cell viability) in order to express the protection gain in relation to the positive control (in %):

Protection gain (%)=% cell viability of test well—% cell viability of irradiated well 8.4. Inhibition of the Release of Type 1 Matrix Metalloproteinase (Protective Effect Against Photo-Ageing)

Type 1 matrix metalloproteinases are interstitial collagenases involved in various physiological mechanisms of tissue remodelling. They are responsible, inter alia, for breaking down the architecture and organisation of cutaneous tissue in response to UV in photo-ageing.

The anti-MMP-1 in vitro test is based on the capacity of keratinocytes to release MMP-1 following stimulation by UV. The HaCaT cells (human immortalized keratinocytes, Life-technology, N° P6110401, Batch 091006), with a passage number below 50, were used in the following cell medium:
DMEM with L-glutamine (Dulbecco's Minimum Essential Medium, PAN BIOTECH. Batch 97487) supplemented with penicillin (100 IU/mL) and streptomycin (100 μg/mL; PAN BIOTECH, Batch 20145241), and with 10% inactivated foetal calf serum (PAN BIOTECH, Batch P440011) at pH 7.2.

A negative control using a saline solution (HBSS, SIGMA) and a positive control using ascorbic acid (25 μM) were set up.

$1 \cdot 10^5$ cells/mL (500 μL/well) were placed in culture in 48-well culture plates and incubated at 37° C. (5% $CO_2$) for 24 h. At the end of this incubation period, the cells were placed in culture with a serum-free medium containing the extracts under test for 1 hour preceding UV stimulation. Irradiation was performed using a Suntest CPS+ simulator (Atlas Material Testing Technology BV, Moussy le Neuf, France) equipped with a xenon lamp (1100 W). The irradiance was set at 750 W/m² with a combined light dose in the order of 15 mJ/cm² for 1 minute. The cells were then re-cultured for 24 hours.

At the end of this incubation period, the supernatant was recovered from the culture in order to measure the MMP-1 released by the cells. The ELISA RayBio Human MMP-1 kit (SIGMA-ALDRICH) was used for this purpose. The optical densities (OD) of each well were then measured at 450 nm using an Infinite M200 Pro plate reader (TECAN). The results obtained were then compared with the untreated well in order to express the protection gain in % relative to the positive control:

$$\text{Protection gain} = 100 - 100 * \frac{(\text{Mean } OD \text{ test well} - \text{Mean } OD \text{ negative control})}{\text{Mean } OD \text{ positive control} - \text{Mean } OD \text{ negative control}}$$

8.5. Activation of Collagen Synthesis

Collagen is a major structural protein of the extra-cellular matrix, playing a role in maintaining the integrity of the skin, in particular giving the skin its longevity and density and imparting a healthy and youthful appearance thereto. The collagen measurement test provides a means of quantifying the soluble collagen in the extra-cellular matrix synthesised within skin cells treated with the extracts to be evaluated. Collagen was detected via the Sircol test (Biocolor, UK), thus using the staining and bonding capacity of Sirius Red on hydroxyproline residues.

Primary human fibroblast cells (Biopredic), with a passage number below 5, were placed in culture in the following medium:
DMEM with L-glutamine (Dulbecco's Minimum Essential Medium, PAN BIOTECH. Batch 5842156) supplemented with penicillin (100 IU/mL) and streptomycin (100 μg/mL; PAN BIOTECH, Batch 9870214), and with 10% inactivated foetal calf serum (PAN BIOTECH, Batch P342518) at pH 7.2.

A negative control using a saline solution (HBSS, SIGMA) and a positive control using ascorbic acid (50 μg/mL) were set up.

$5 \cdot 10^5$ cells/mL (1000 μL/well) were placed in culture in 24-well culture plates and incubated at 37° C. (5% $CO_2$) for 24 until confluence was reached. At the end of this incubation period, the cells were placed in culture in a serum-free medium containing the extracts under test for 72 hours at different concentrations. The detection protocol using the Sircol method was then applied. More precisely, the culture medium is collected for centrifuging with 100 μl of polyethylene glycol in a TRIS-HCl buffer (pH 7.6) then incubated overnight at between 0 and 4° C. The samples were then centrifuged at 12000 rpm for 10 minutes in order to recover the supernatants for the addition of 1 ml of Sircol dye reagent. After agitation for 30 minutes at ambient temperature, the tubes were re-centrifuged at 12000 rpm for 10 minutes. Following removal of the supernatant, 750 μl of a reagent containing a mixture of acetic acid/sodium chloride/detergent were added. After re-centrifuging, the supernatant was removed for the addition of 250 μl of an alkaline reagent (sodium hydroxide at 0.5 M). Following agitation, 200 μl were transferred from each well to a 96-well microplate in order to measure the absorbances at 555 nm using an Infinite M200 Pro microplate reader (TECAN). The results obtained were then compared with the untreated well in order to express the protection gain in relation to the positive control (in %):

$$\text{Collagen gain (\%)} = \frac{(\text{mean } OD \text{ test well} - \text{mean } OD \text{ negative control}) - (\text{mean } OD \text{ positive control} - \text{mean } OD \text{ negative control})}{(\text{mean } OD \text{ positive control} - \text{mean } OD \text{ negative control})}$$

FIGURES

Figure 6:
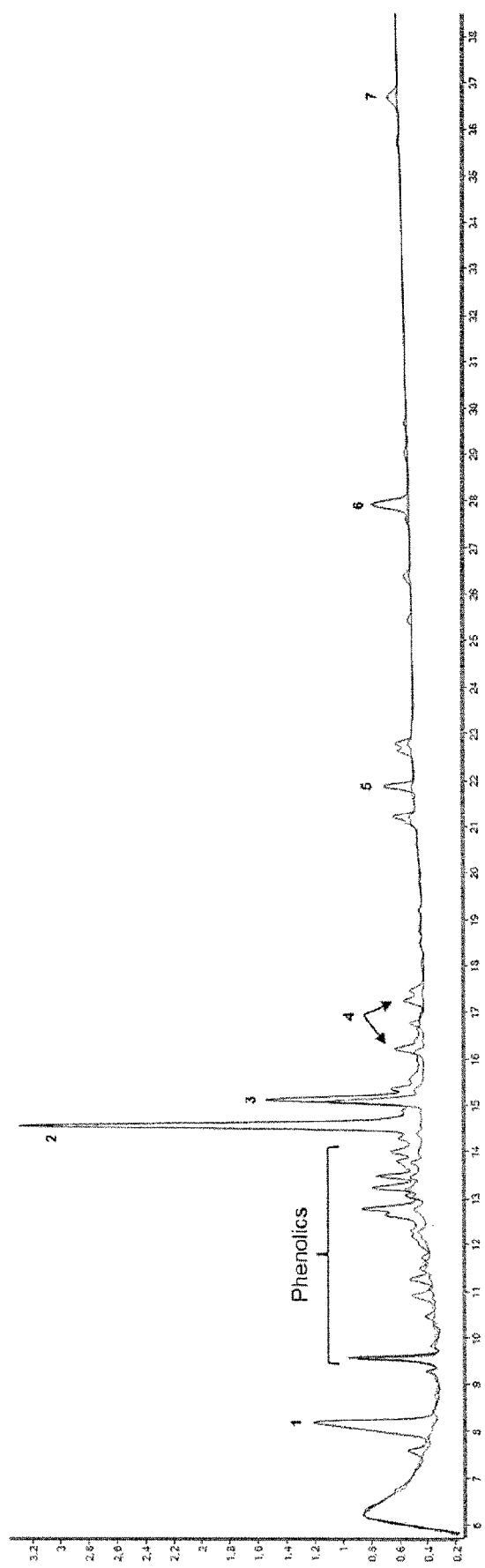

FIG. 6 shows the chromographic profile (LC/UV, 230 nm) obtained from the liquid extracts of rosemary obtained in Example 7 as described below, where 1 is an unidentified compounds, 2 is rosmarinic acid, 3 is luteolin-3-O-glucuronide, 4 is luteolin-3'-(4"-acetylglucuronide) isomer, 5 is rosmanol, 6 is carnosol and 7 is methyl carnosate. The black trace being the results obtained when the eutectic solvent was used for the extraction and the grey trace being the result obtained when water:glycerol was used for the extraction.

Figure 7:
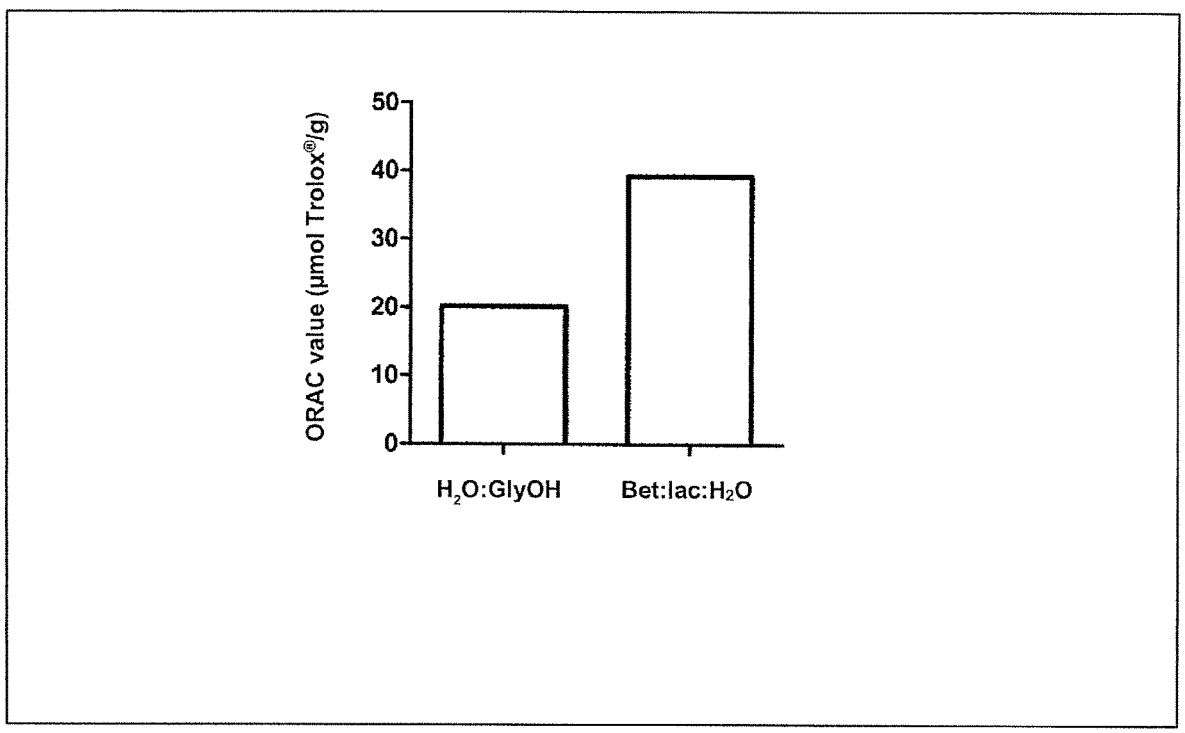

FIG. 7 shows the antioxidant capacities of liquid extracts of rosemary obtained in Example 7 as described below, expressed as ORAC value (pmol Trolox eq/g of sample) for Oxygen Radical Absorbance Capacity.

Figure 8:
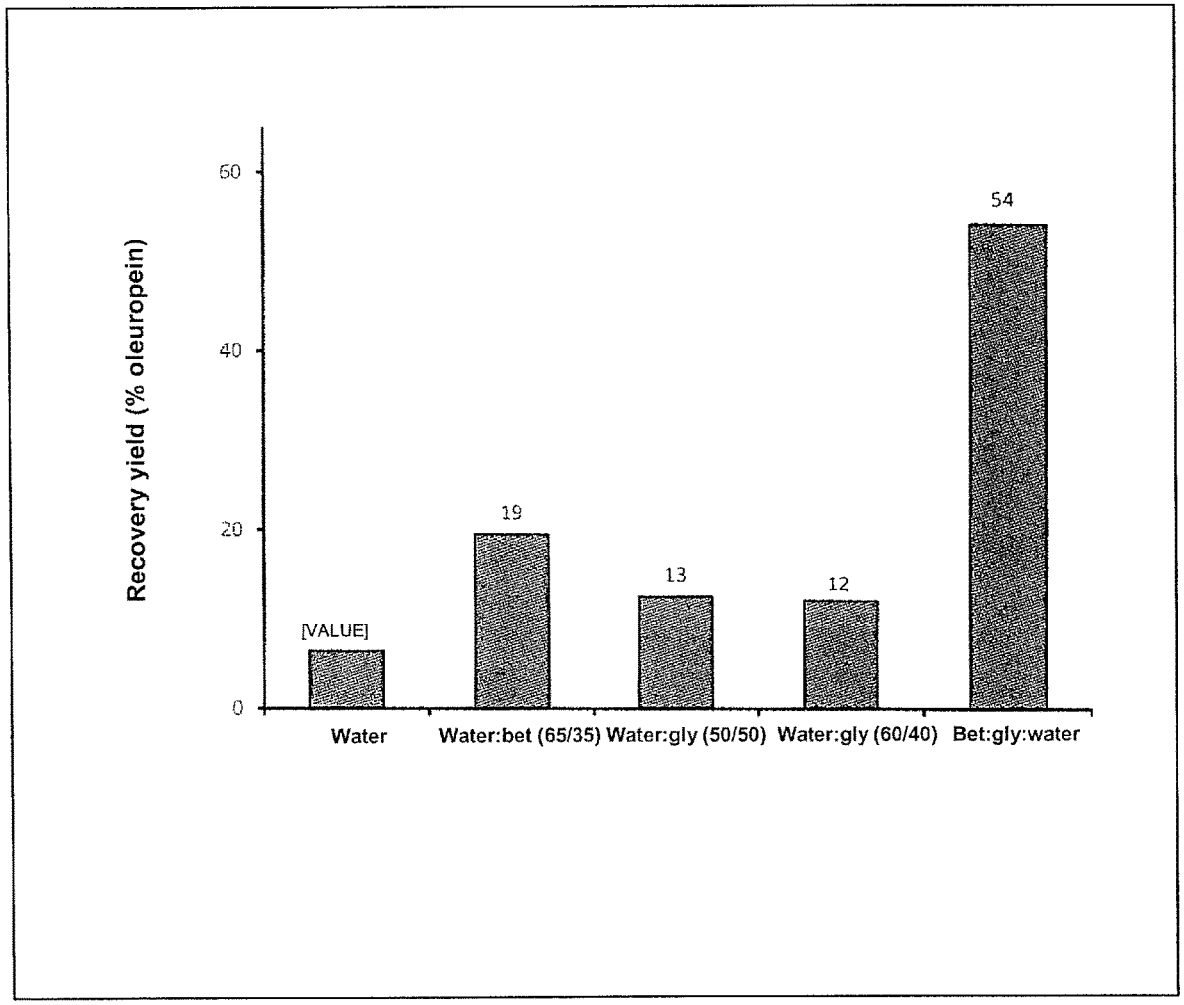

FIG. 8 shows the recovery yield of oleuropein from olive leaves depending on the extracting fluid composed of water and/or betaine and/or glycerol as described in Example 8 below.

Figure 9:
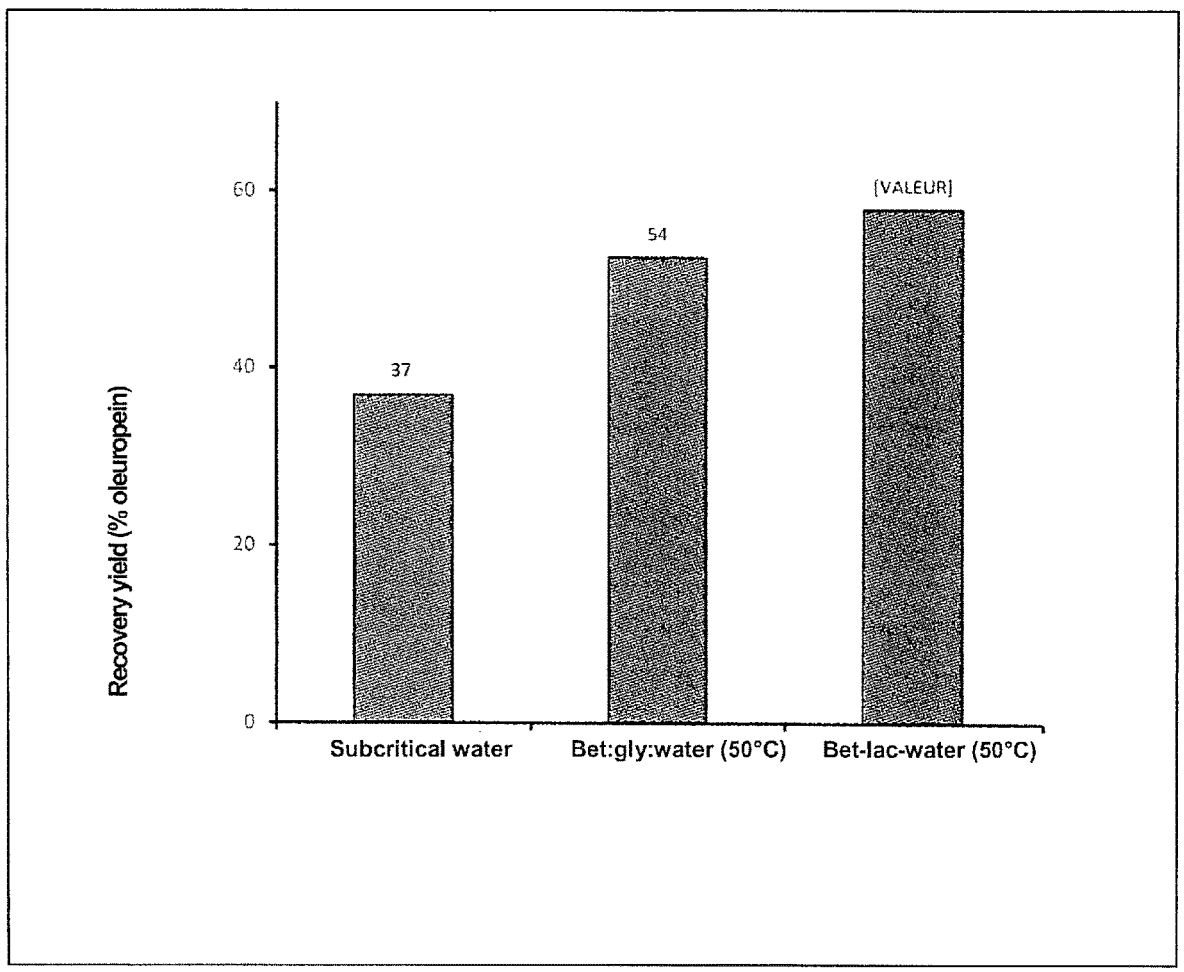

FIG. 9 shows the recovery yield of oleuropein from olive leaves using subcritial water as described in Example 10.

Figure 10:
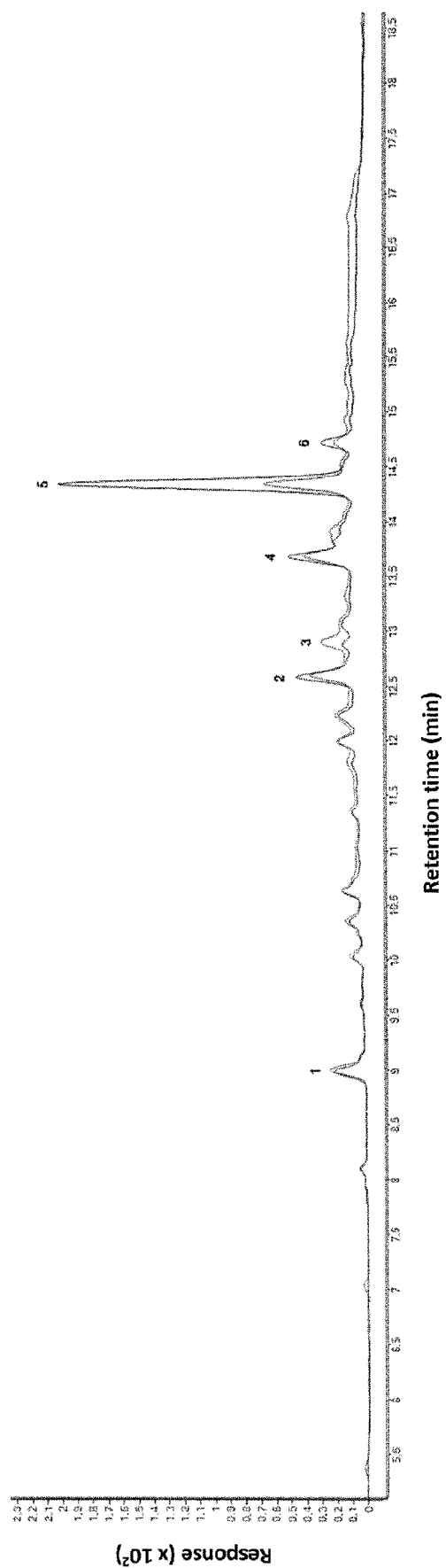

FIG. 10 shows the chromatographic profiles (LC/UV, 280 nm) of liquid extracts of olives leaves obtained in Example 11 using either betaine:glycerol:water or hydroglycerin as the extraction solvent. 1 is hydroxytyrosol, 2 is Luteolin-7-O-glucoside, 3 is Unidentified, 4 is Luteolin-glucoside, 5 is Oleuropein and 6 is Oleuropein isomer. The black trace being the results obtained when the eutectic solvent was used for the extraction and the grey trace being the result obtained when water:glycerol was used for the extraction.

Figure 11:
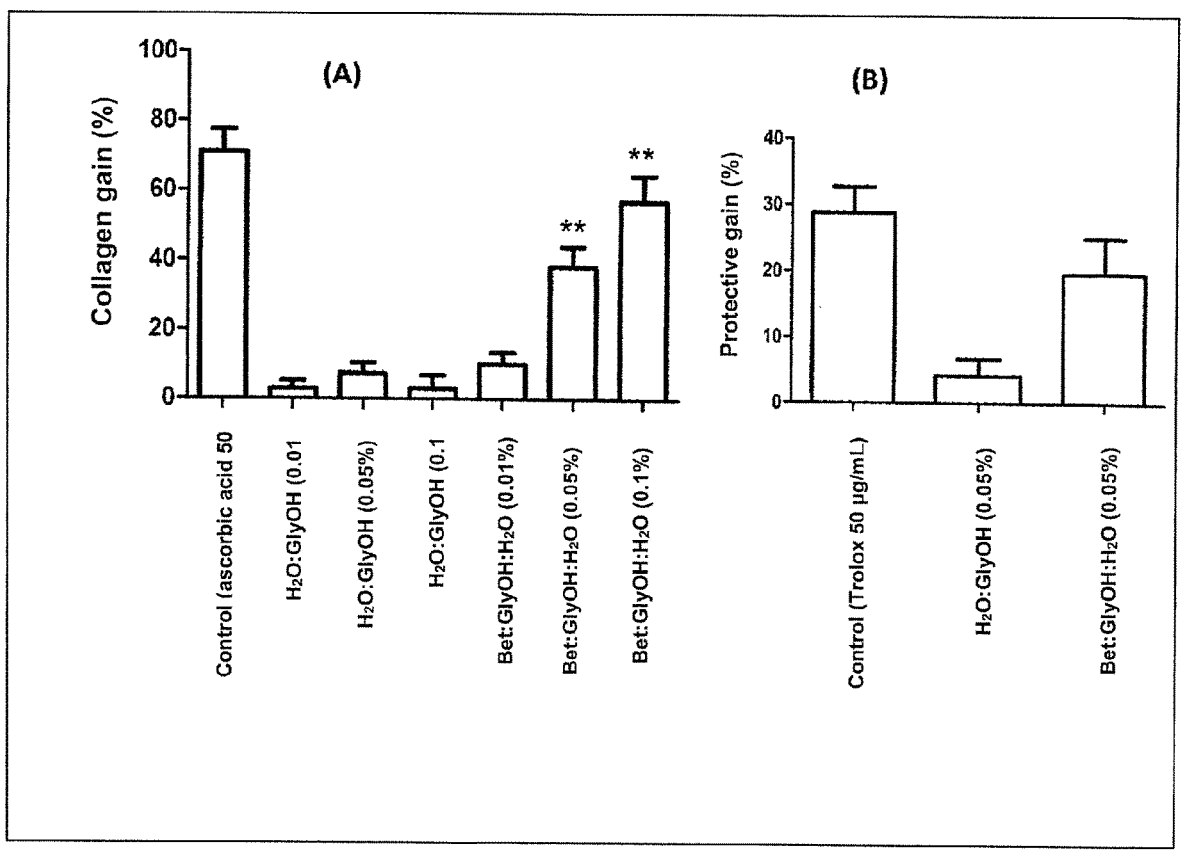

FIGS. 11A and 11B show the collagen gain (A) and protective gain (B) achieved by cells following cell incubation with liquid extracts of olive leaves obtained in Example 11 using different extractions solvents. $*p<0.05$; $p<0.01$, $*p<0.001$, t-test.

Figure 12:
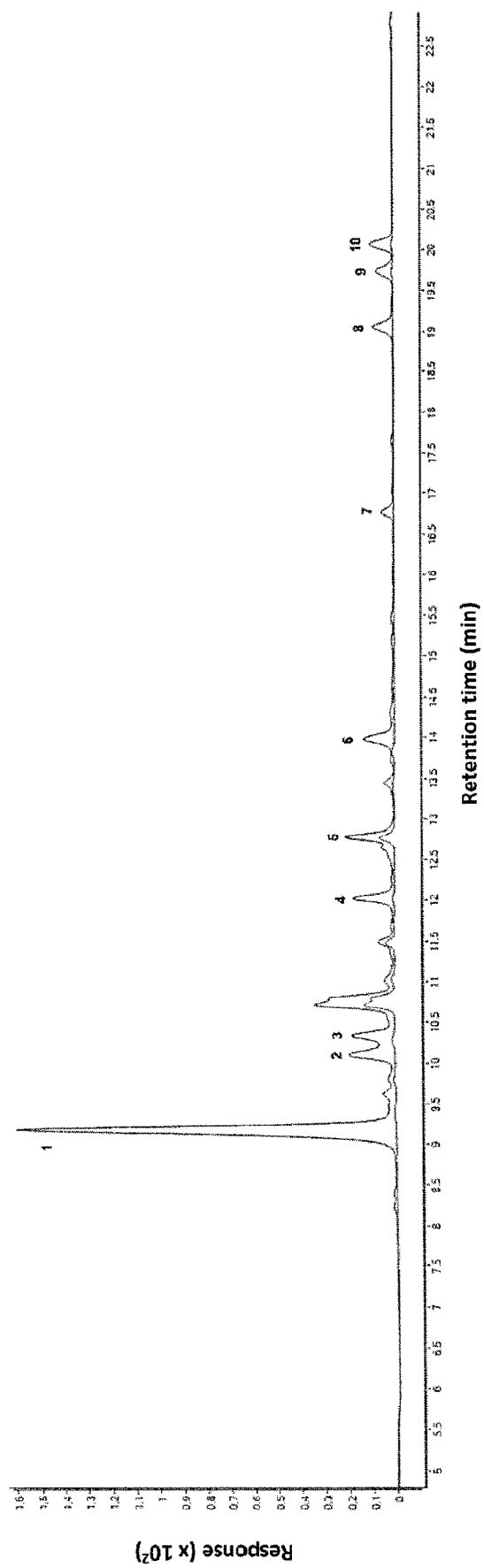

FIG. 12 shows the chromatographic profiles (LC/UV, 350 nm) of liquid extracts of cherry blossom obtained in Example 12 using either betaine:glycerol:water, betaine:lactic acid:water or hydroglycerin as the extraction solvent. 1 is Caffeoyl glucoside, 2 is Chlorogenic acid, 3 is Coumaroyl glucoside, 4 is Rutin, 5 is Kaempferol rutinoside, 6 is Dicaffeoyl quinic acid, 7 is Unidentified, 8 is Isorhamnetin, 9 is Flavonoid C17H14O7 and 10 is Flavonoid C18H16O8. The black trace being the results obtained when eutectic solvents were used for the extraction and the grey trace being the result obtained when water:glycerol was used for the extraction.

FIGS. 13A, 13B, 13C and 13D show post UV irradiation photo-protection (A), inhibition of the release of type 1 matrix metalloproteinases (MMP-1) (B), anti-inflammatory activity vis-à-vis TNFα (C), collagen synthesis (D) following cell exposure to liquid extracts of cherry blossom based on the liquid extracts of cherry blossom obtained in Example 12. $*p<0.05$; $p<0.01$, $*p<0.001$, t-test.

FIGS. 14A, 14B, 14C and 14D show post UV irradiation photo-protection through the tight-junction protein ZO-1 synthesis (A), loricrin synthesis (B), and antioxidant activity prior to the cell recruitment of DJ-1/NRF2 pathway (C and D) following human skin explant exposure to liquid extracts of cherry blossom based on the liquid extracts of cherry blossom obtained in Example 12. $*p<0.05$; $p<0.01$, $*p<0.001$, t-test.

Figure 15:
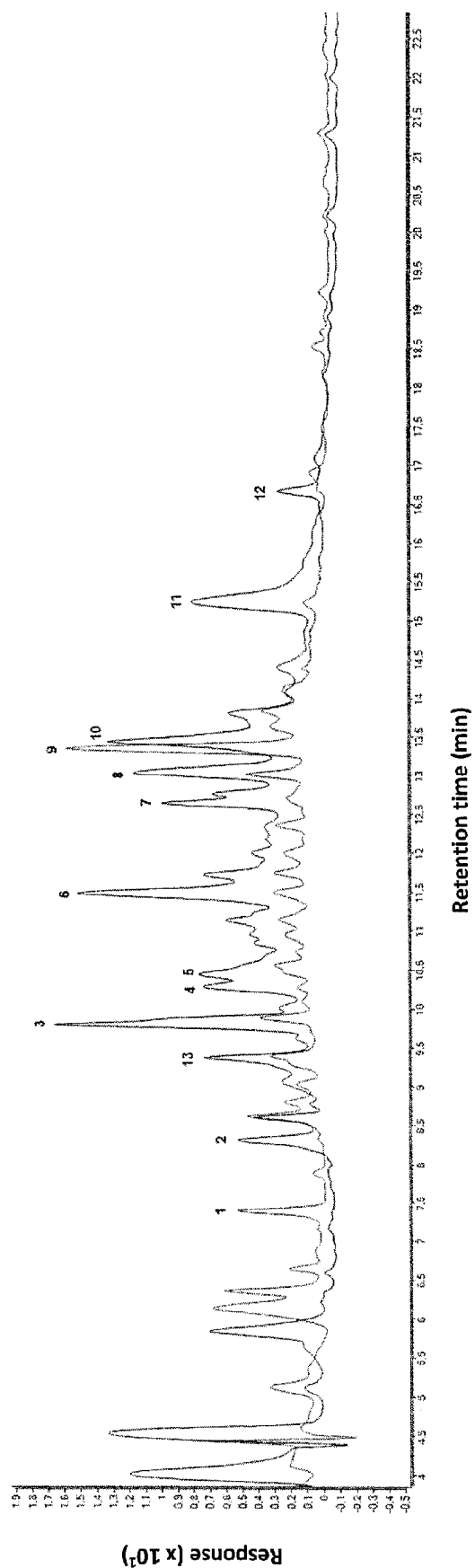

FIG. 15 shows the chromatographic profiles (LC/UV, 280 nm) of liquid extracts of horsetail obtained in Example 13 using either betaine:lactic acid:water or hydroglycerin as the extraction solvent. 1 is an Unidentified phenolic, 2 is an Unidentified alkaloid, 3 is Kaempferol dihexoside rhamnoside, 4 is Caffeoyl tartaric acid, 5 is Caffeoyl tartaric acid isomer, 6 is Phaseolic acid, 7 is Gossupitrin, 8 is Protogenkwanin-4'-O-glucoside, 9 is Coumaric acid, 10 is Ferulic acid derivative, 11 is Unidentified, 12 is Unidentified and 12 is Kaempferol trihexoside rhamnoside. The black trace being the results obtained when eutectic solvents were used for the extraction and the grey trace being the result obtained when water:glycerol was used for the extraction.

Figure 16:
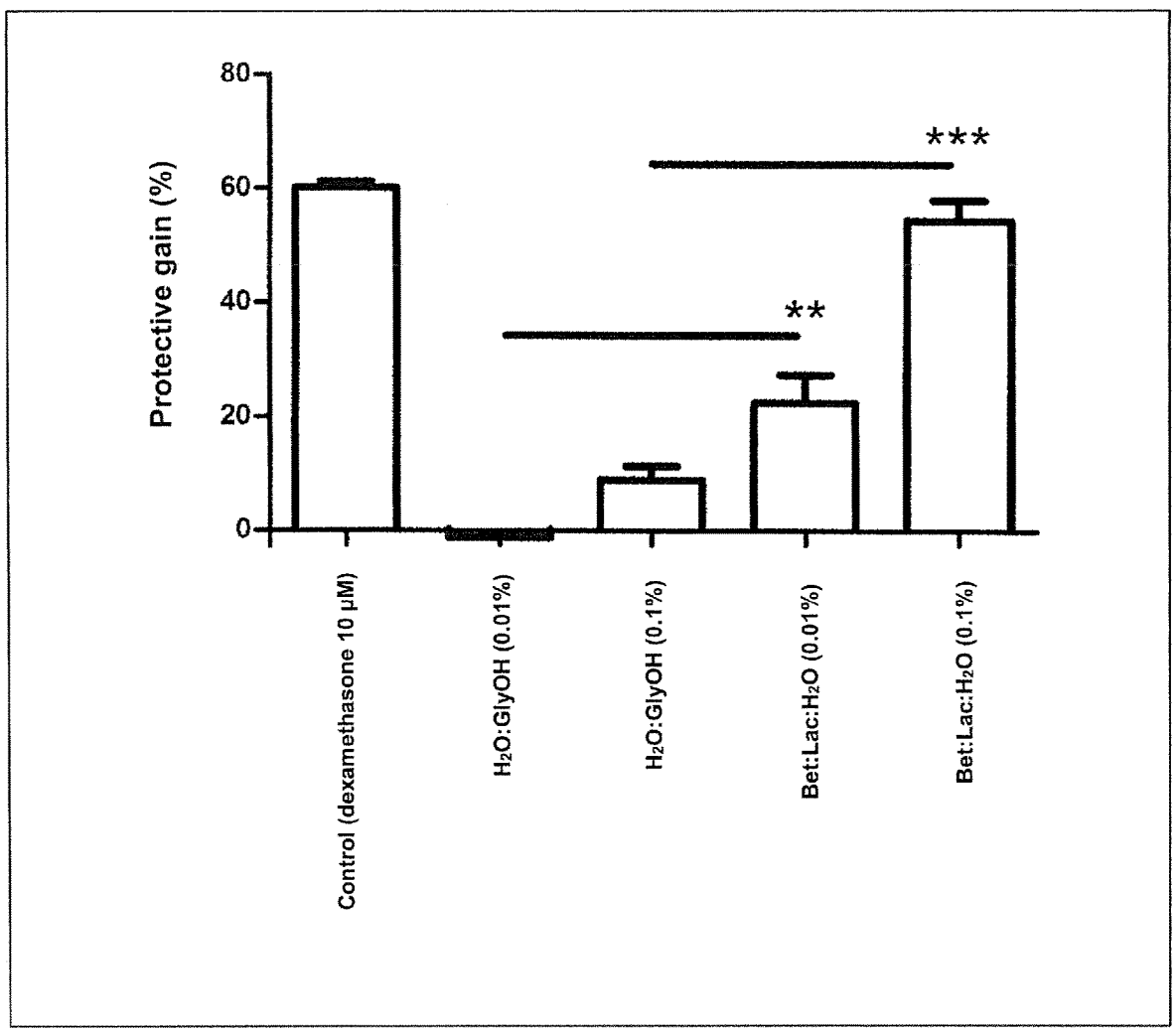

FIG. 16 shows the anti-inflammatory activity of horsetail extracts obtained in Example 13 using different extractions solvents by showing the inhibition of the release of TNF-alpha following UV exposure of keratinocytes HaCaT.

Figure 17:
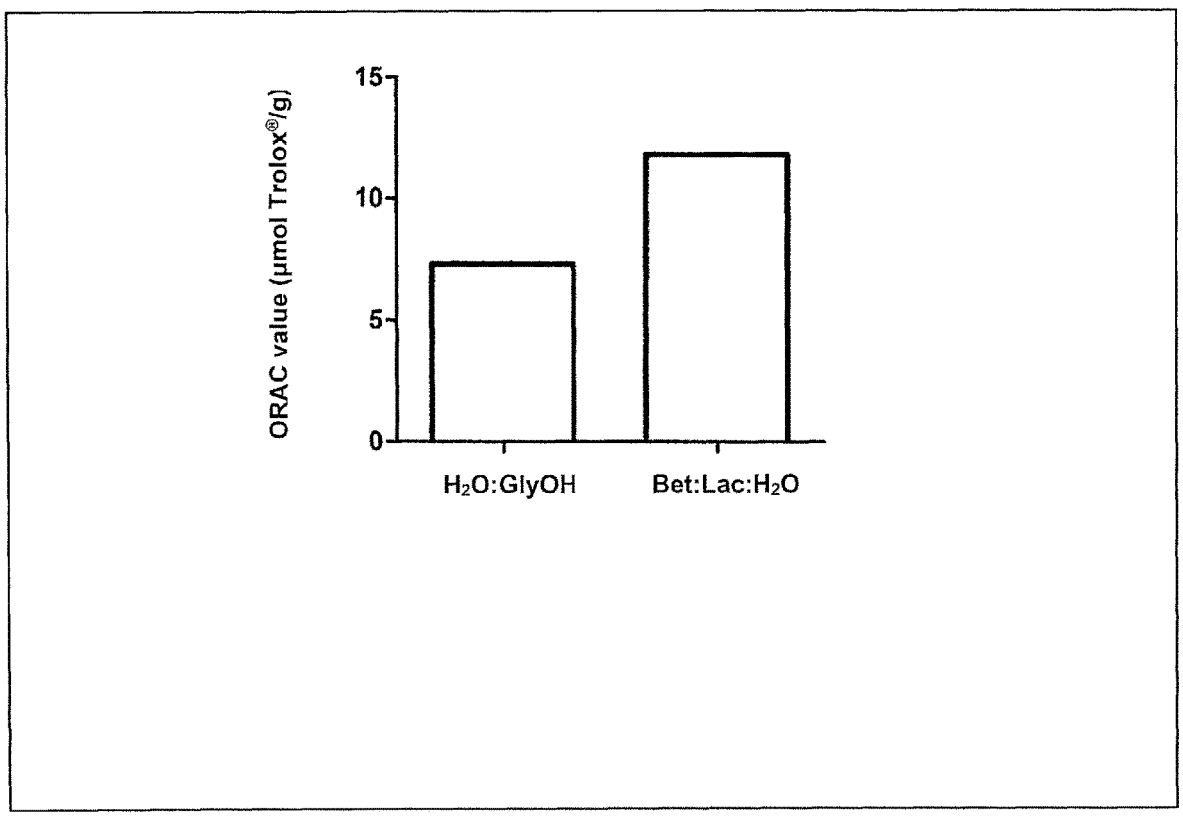

FIG. 17 shows the antioxidant capacities of liquid extracts of horsetail obtained in Example 13 using different extractions solvents expressed as ORAC value (pmol Trolox eq/g of sample) for Oxygen Radical Absorbance Capacity.

Figure 18:
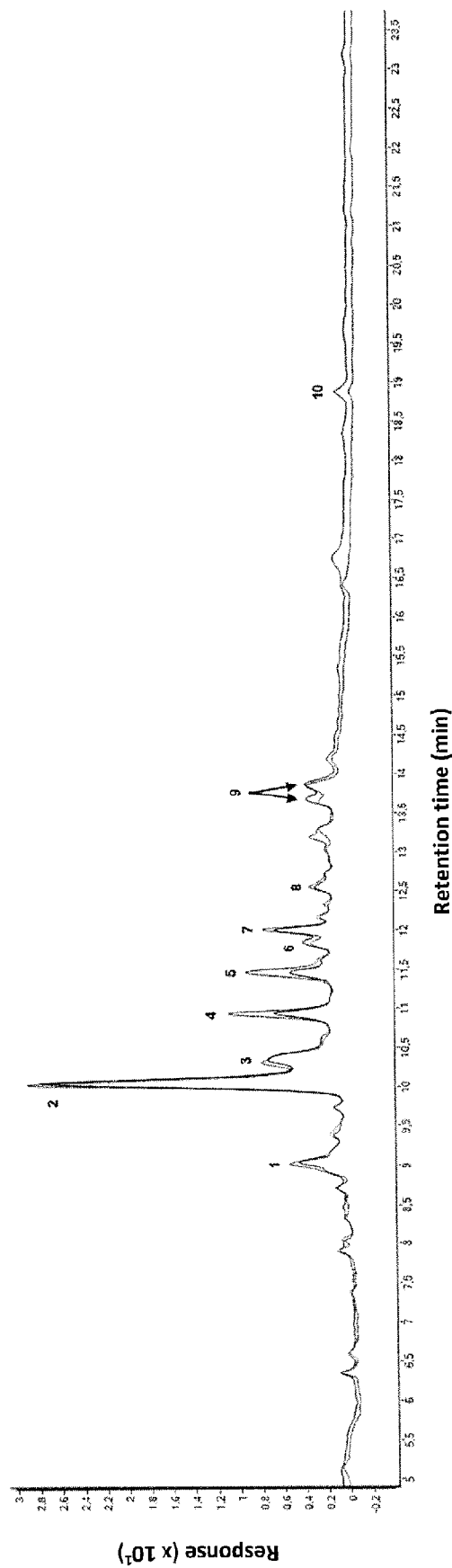

FIG. 18 shows the chromatographic profiles (LC/UV, 280 nm) of liquid extracts of crithmum (rock samphire) obtained in Example 14 using either betaine:glycerol:water or hydroglycerin as extraction solvent. 1 is 3-Caffeoylquinic acid, 2 is 5-Caffeoylquinic acid, 3 is 4-Caffeoylquinic acid, 4 is 1-Caffeoylquinic acid, 5 is 5-p-Coumaroylquinic acid, 6 is 5-Feruloylquinic acid, 7 is Ruitin, 8 is Quercetin-3-O-glucoside, 9 is Dicaffeoylquinic acid isomer and 10 is an Unidentified flavone. The black trace being the results obtained when eutectic solvents were used for the extraction and the grey trace being the result obtained when water:glycerol was used for the extraction.

Figure 19:
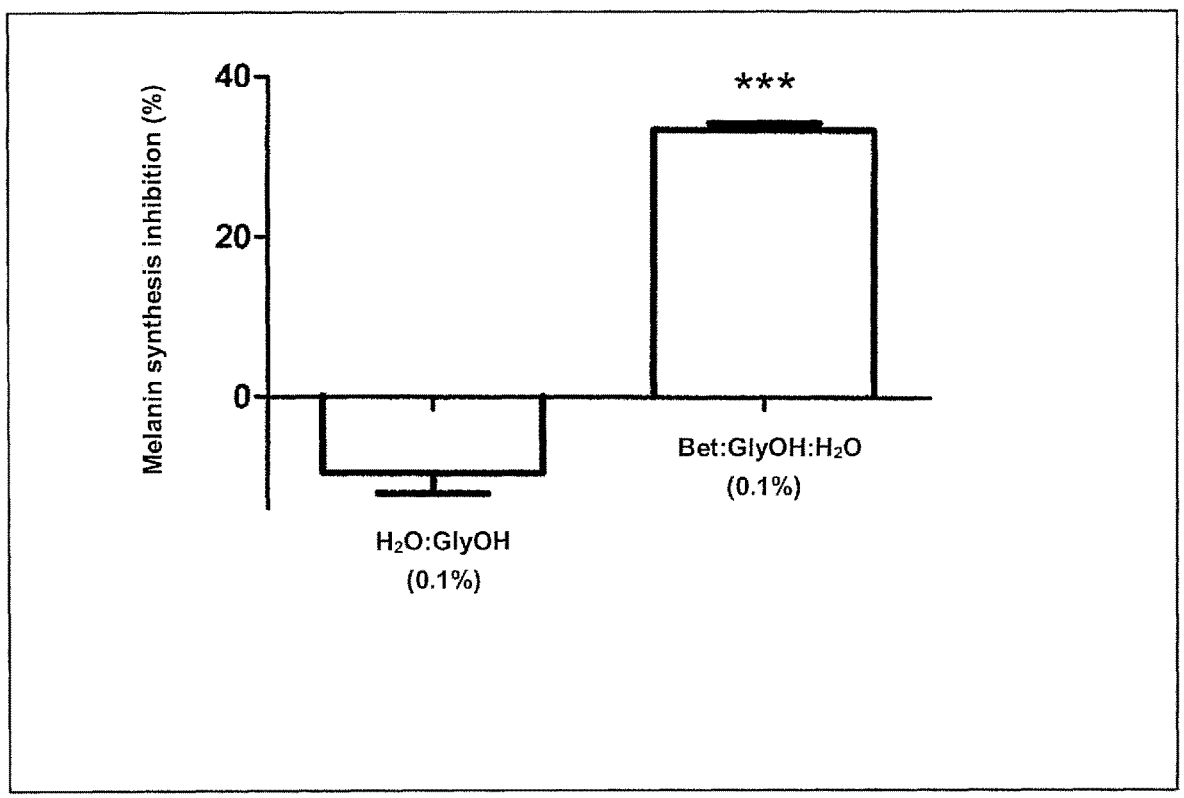

FIG. 19 shows melanin synthesis inhibition following exposure to liquid extracts of crithmum obtained in Example 14 using different extraction solvents on melanocytes of lightly pigmented human skin (stimulated in the presence of 1 mM of L-tyrosine). $***\ p<0.0001$, t-test.

Figure 20:
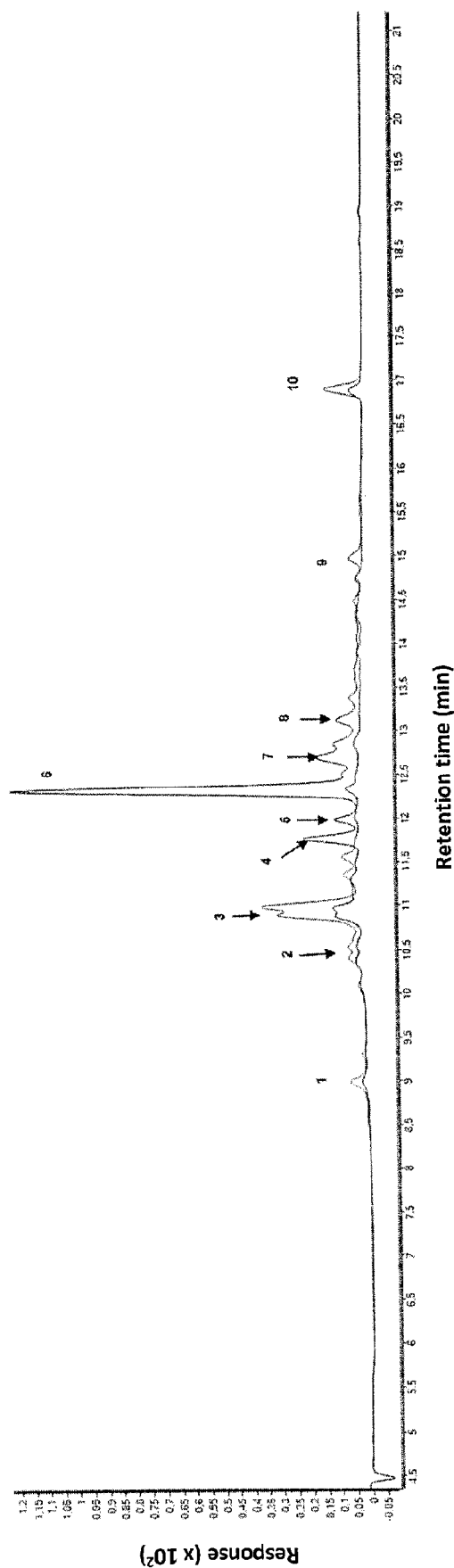

FIG. 20 shows the chromatographic profiles (LC/UV, 350 nm) of liquid extracts of plantain obtained in Example 15 using either betaine:glycerol:water or hydroglycerin as extraction solvent. 1 is Cistanoside F, 2 is Hydroxyverbascoside, 3 is Dihydroxyverbascoside, 4 is Hydroxyverbascoside isomer, 5 is Phenylethanoid glycoside, 6 is Verbascoside, 7 is Isoverbascoside, 8 is Luteolin diglucuronide, 9 is Luteolin glucuronide and 10 is Scuttelarein. The black trace being the results obtained when eutectic solvents were used for the extraction and the grey trace being the result obtained when water:glycerol was used for the extraction.

Figure 21:
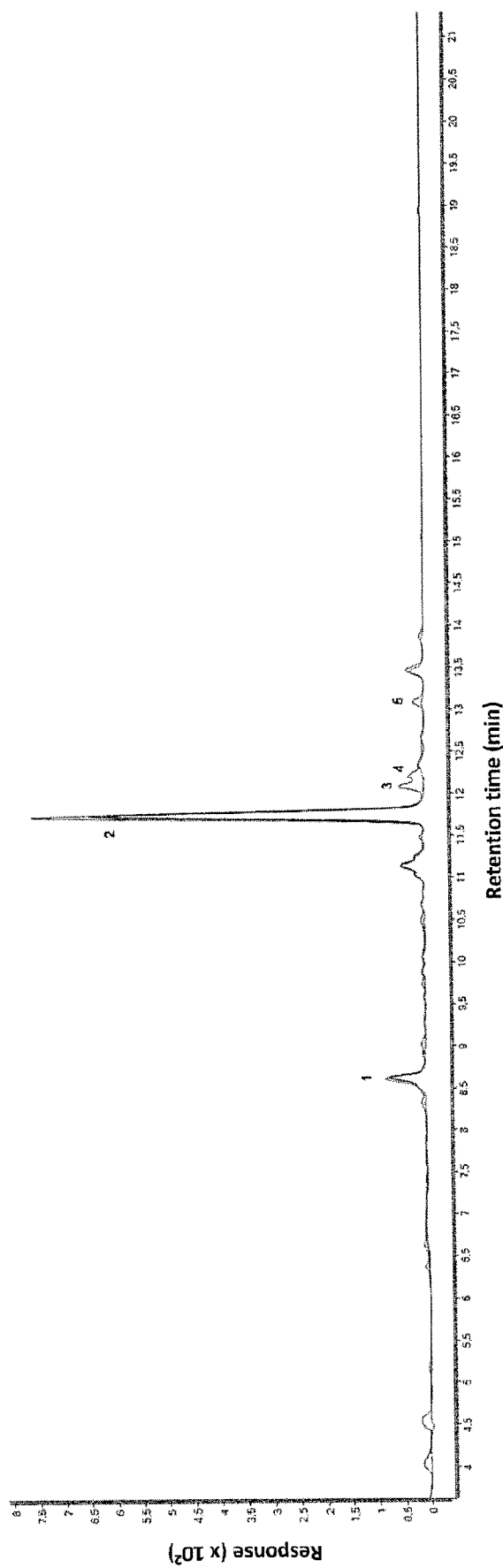

FIG. 21 shows the chromatographic profiles (LC/UV, 350 nm) of liquid extracts of saffron flowers obtained in Example 16 using either betaine:lactic acid:water or hydroglycerin as extraction solvent. 1 is Kaempferol-3-O-sophoroside-7-O-glucoside, 2 is Kaempferol-3-O-sophoroside, 3 is Kaempferol-3-O-lactyl-sophoroside, 4 is Kaempferol-3-O-lactyl-sophoroside isomer and 5 is Kaempferol glycosyl-glyceryl rhamnosyl. The black trace being the results obtained when eutectic solvents were used for the extraction and the grey trace being the result obtained when water:glycerol was used for the extraction.

Figure 22:
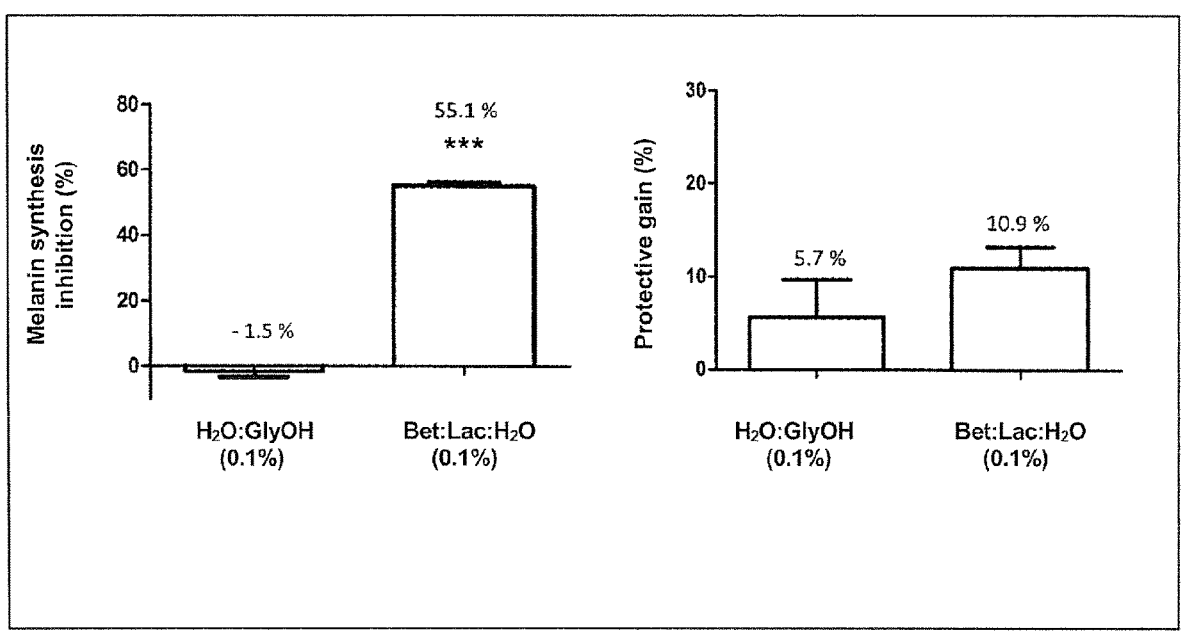

FIG. 22 shows the inhibition of melanin synthesis (A) and of release of type 1 matrix metalloproteinases (MMP-1) (B) by liquid extracts of saffron flowers obtained in Example 16 using different extraction solvents (following UV exposure of cells). *** $p<0.001$, t-test.

Figure 23:
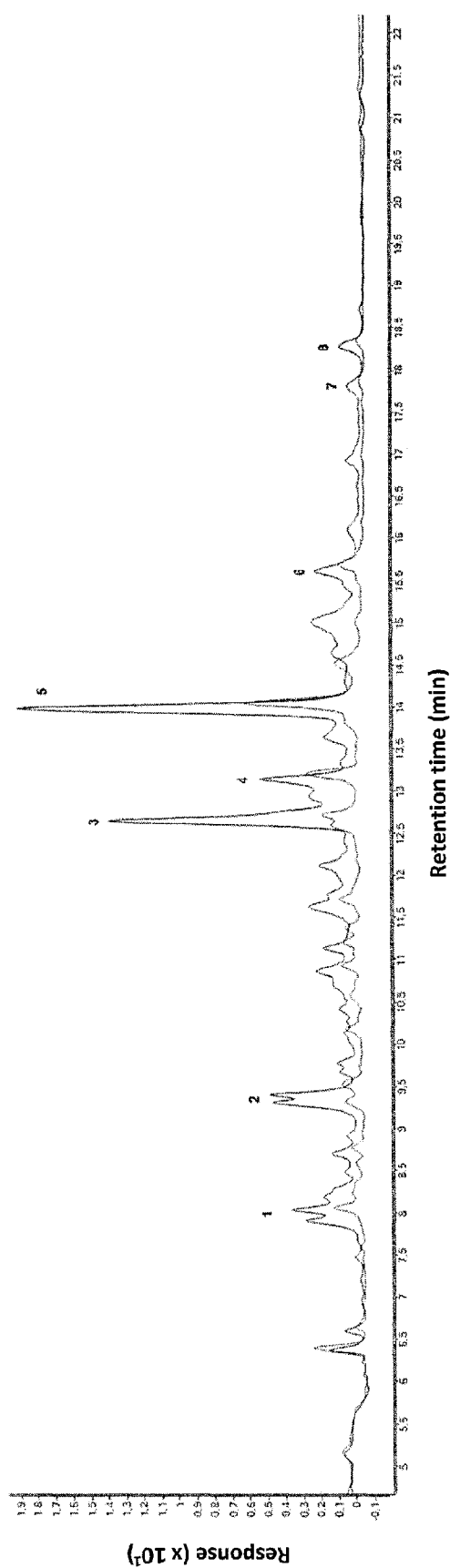

FIG. 23 shows the chromatographic profiles (LC/UV, 280 nm) of liquid extracts of rose of Jericho obtained in Example 17 using either betaine:glycerol:water, betaine:lactic acid:water or hydroglycerin as extraction solvent. 1 is Unidentified, 2 is Protocatechuic acid, 3 is Picein, 4 is unidentified, 5 is Taxifolin, 6 is Taxifolin methyl ether, 7 is Silybin and 8 is Isosilybin. The black trace being the results obtained when eutectic solvents were used for the extraction and the grey trace being the result obtained when water:glycerol was used for the extraction.

Figure 24:
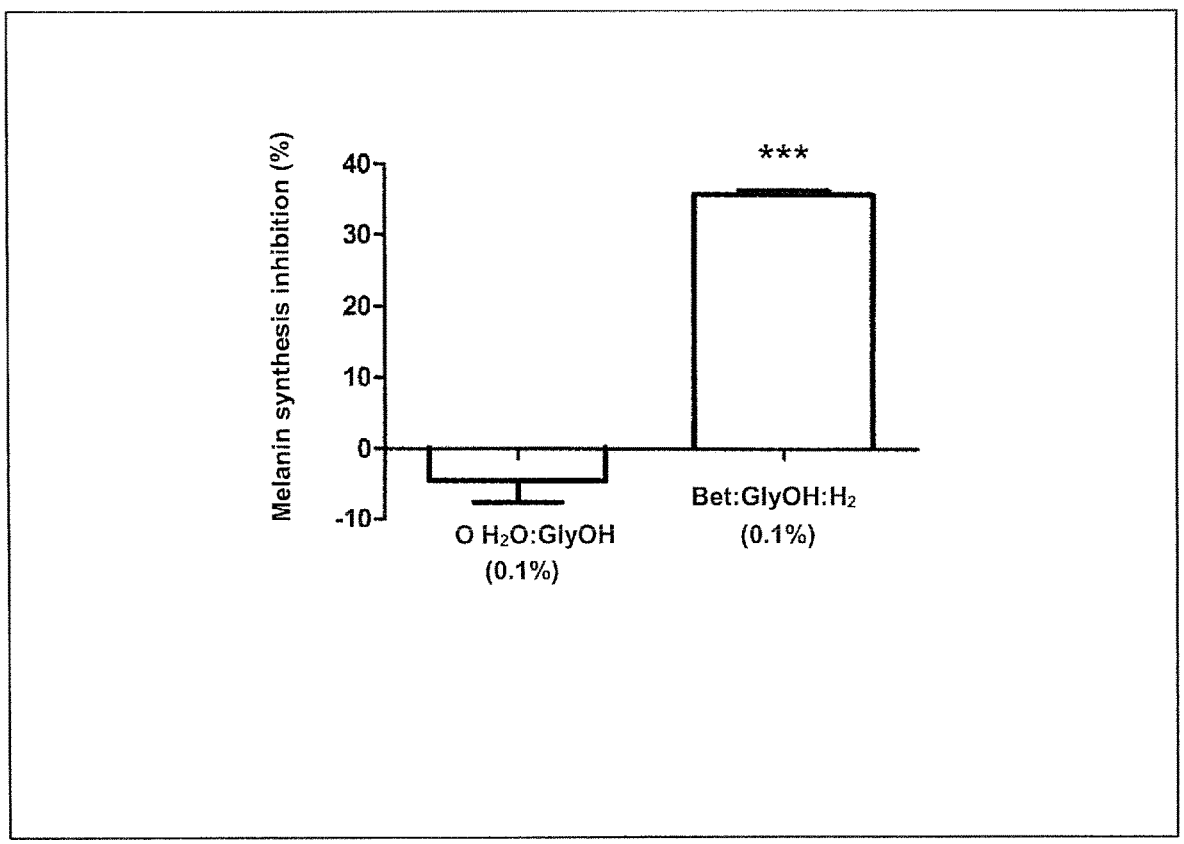

FIG. 24 shows the melanin synthesis inhibition following exposure to liquid extracts of rose of Jericho obtained in Example 17 using different extraction solvents on melanocytes of lightly pigmented human skin (stimulated in the presence of 1 mM of L-tyrosine). *** $p<0.001$, t-test.

EXAMPLES

The following examples are merely illustrative examples of the processes of the invention described herein. All equipment, reagents and solvents used were standard laboratory equipment, e.g. glassware, heating apparatus and HPLC apparatus.

It must be borne in mind that these examples show an extraction synergy for a betaine:hydrogen bond donor ratio of 2:3. However, when the values obtained are rounded to integers, the ratio 2:3 becomes 1:2.

Example 1. Molar Ratio Criticality of the Betaine:Lactic Acid Binary Mixture

TABLE 1

Visual appearance of betaine:lactic acid binary mixtures depending on molar ratio

| Betaine (%) | Lactic acid (%) | Clarity |
|---|---|---|
| 70 | 30 | Immediate formation of a precipitate |
| 60 | 40 | Immediate formation of a precipitate |
| 50 | 50 | Formation of crystals after one week |
| 40 | 60 | Liquid and clear |
| 30 | 70 | Liquid and clear |
| 20 | 80 | Formation of crystals after one day |

Figure 1:
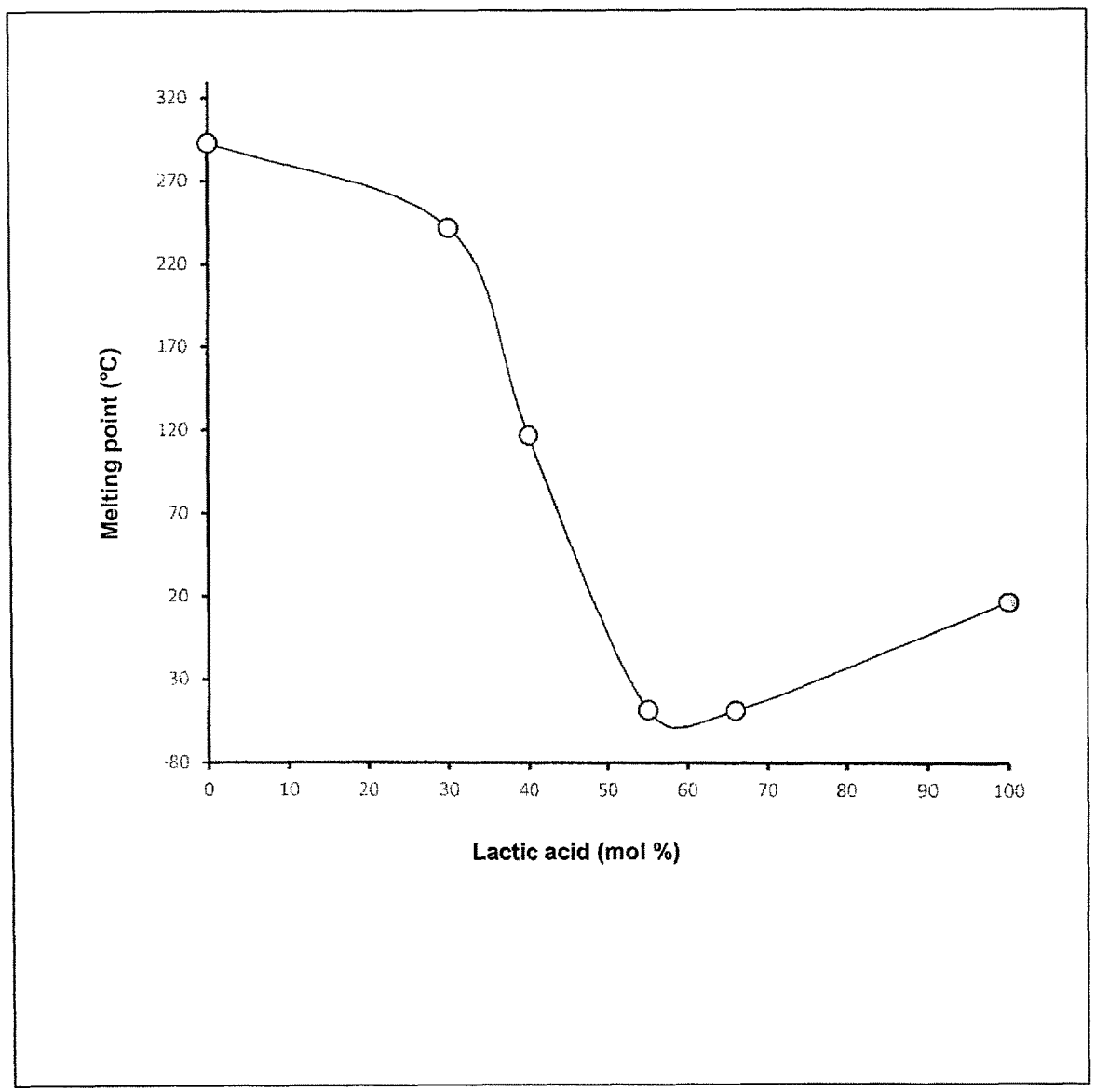
FIG. 1 shows the results obtained from Example 1 as described below as a binary phase diagram between betaine monohydrate and lactic acid (hydrogen bond donor). The proportions of betaine monohydrate and lactic acid are given in mole %.

When the molar proportions of betaine and lactic acid are varied, a narrow range of composition between 40:60 and 30:70%, respectively, is observed for which the mixture is clear. Below and above this threshold, the mixture exhibits characteristics of unstable media with crystal formation immediately after mixing (betaine:lactic acid molar ratios of 70:30, 60:40 and 50:50) or after one week's storage at ambient temperature (ratio 20:80). It is interesting to note that this composition range corresponds exactly to the appearance of a maximum lowering of the melting point on the phase diagram of the mixture (FIG. 1). This maximum lowering (or eutectic point) is due to the complex phenomenon of eutectigenesis of which the mechanism of action has never to our knowledge been elucidated for mixtures of betaine and hydrogen bond donors. We can nevertheless advance the hypothesis that supramolecular assemblages formed by the establishment of hydrogen and/or ionic bonds between betaine and lactic acid are conducive to a rearrangement of the molecule network by increasing the volume of empty space. FIG. 1 shows clearly that eutectigenesis occurs for a betaine:lactic acid ratio of around 33:66, which implies that a molecule of betaine interacts in a non-covalent manner with two molecules of lactic acid. Thus it will be understood that a ratio deviating from this equilibrium leads to destabilisation of the mixture and to a considerable increase in the melting point. For extractive purposes, it is therefore necessary to use molar mixtures precisely between 50:50% and 30:70%, preferably between 40:60 and 30:70% of betaine and lactic acid, respectively. These molar ratios have melting points between ambient temperature and −40° C. and are preferably liquid and clear at ambient temperature and at 50° C., which is a prerequisite for the use thereof as extracting fluid.

Example 2. Molar Ratio Criticality of the Betaine:Glycerol Binary Mixture

TABLE 2

Visual appearance of betaine:glycerol binary mixtures depending on molar ratio

| Betaine (%) | Glycerol (%) | Visual appearance |
|---|---|---|
| 70 | 30 | Immediate formation of precipitate then crystallisation |
| 60 | 40 | Immediate formation of precipitate then crystallisation |
| 50 | 50 | Immediate formation of precipitate then crystallisation |
| 40 | 60 | Liquid and clear |
| 30 | 70 | Liquid and clear |
| 20 | 80 | Liquid and clear |

Figure 2:
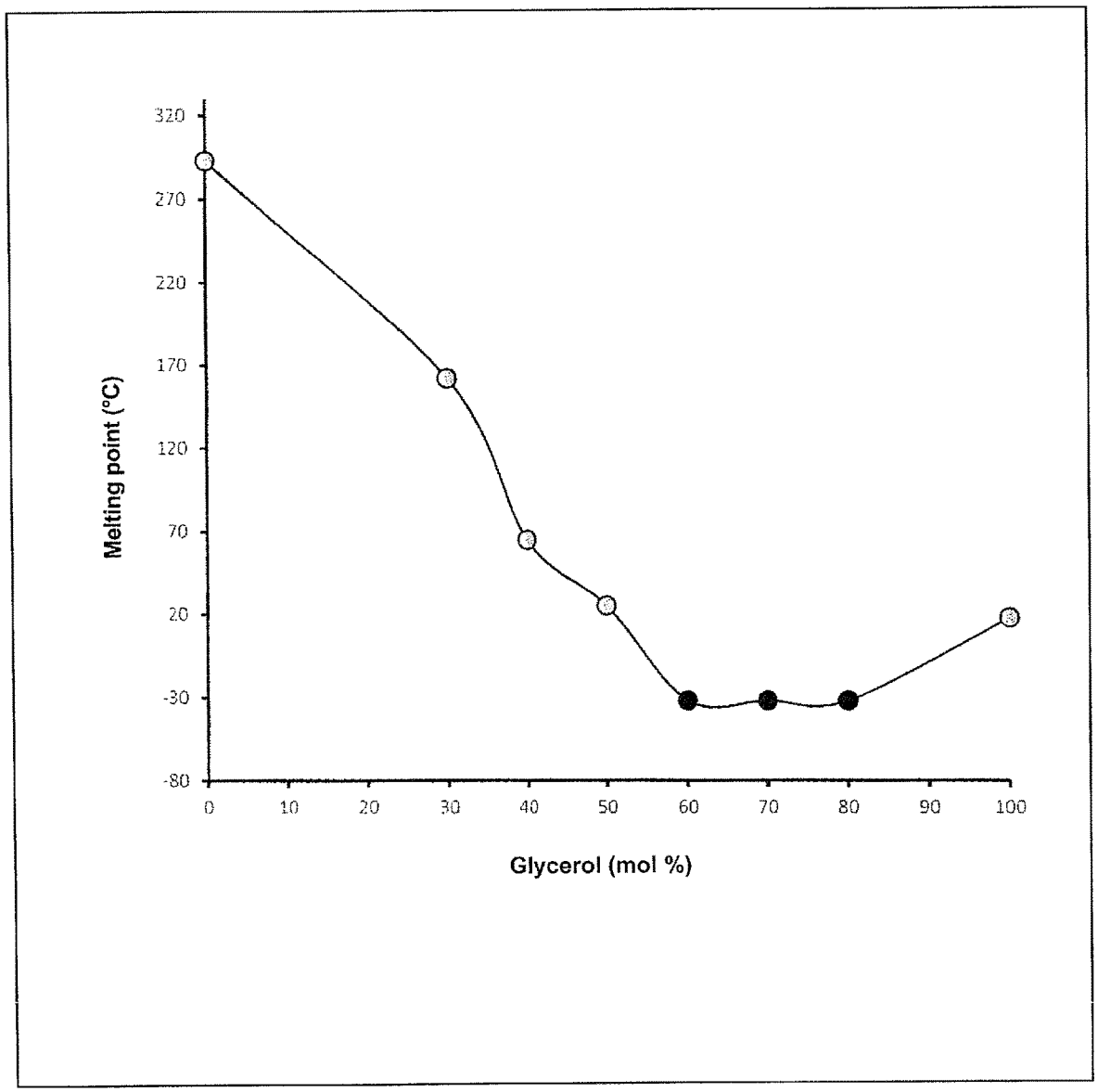
FIG. 2 shows the results obtained from Example 2 as described below as a binary phase diagram between betaine monohydrate and glycerol (hydrogen bond donor). The proportions of betaine monohydrate and glycerol are given in mole %.

Macroscopic observation of betaine:glycerol mixtures with different molar ratios shows that a minimum of 60% glycerol is necessary to obtain a clear mixture which can be used in solid/liquid extraction (Table 2). Betaine:glycerol molar ratios of 70:30, 60:40 and 50:50 all lead to the immediate formation of solid particles visible to the naked eye, which destabilise the medium then rapidly crystallise. These results are also confirmed by the phase diagram of this mixture which indicates a eutectic point for a betaine:glycerol ratio of 40:60 respectively (FIG. 2). The criticality of eutectigenesis to form a clear mixture is not fortuitous and probably results—as in Example 1—from supramolecular assemblages characteristic of eutectic mixtures which can only form in precise quantitative ratios between the molecular species involved. In the example given here, one molecule of betaine monohydrate interacts with two glycerol molecules, as shown in FIG. 2. Finally, the addition of 60% glycerol makes it possible to lower the melting point of the betaine and to obtain a liquid eutectic mixture down to −40° C.

Example 3. Absence of Molar Ratio Criticality of the Betaine:Citric Acid Binary Mixture

TABLE 3

Visual appearance of betaine:citric acid binary mixtures depending on molar ratio

| Betaine (%) | Citric acid (%) | Clarity |
| --- | --- | --- |
| 70 | 30 | Formation of crystals after one week |
| 60 | 40 | Formation of crystals after one week |
| 50 | 50 | Formation of crystals after one week |
| 40 | 60 | Formation of crystals after one week |
| 30 | 70 | Formation of crystals after one week |
| 20 | 80 | Immediate formation of crystals |

Figure 3:
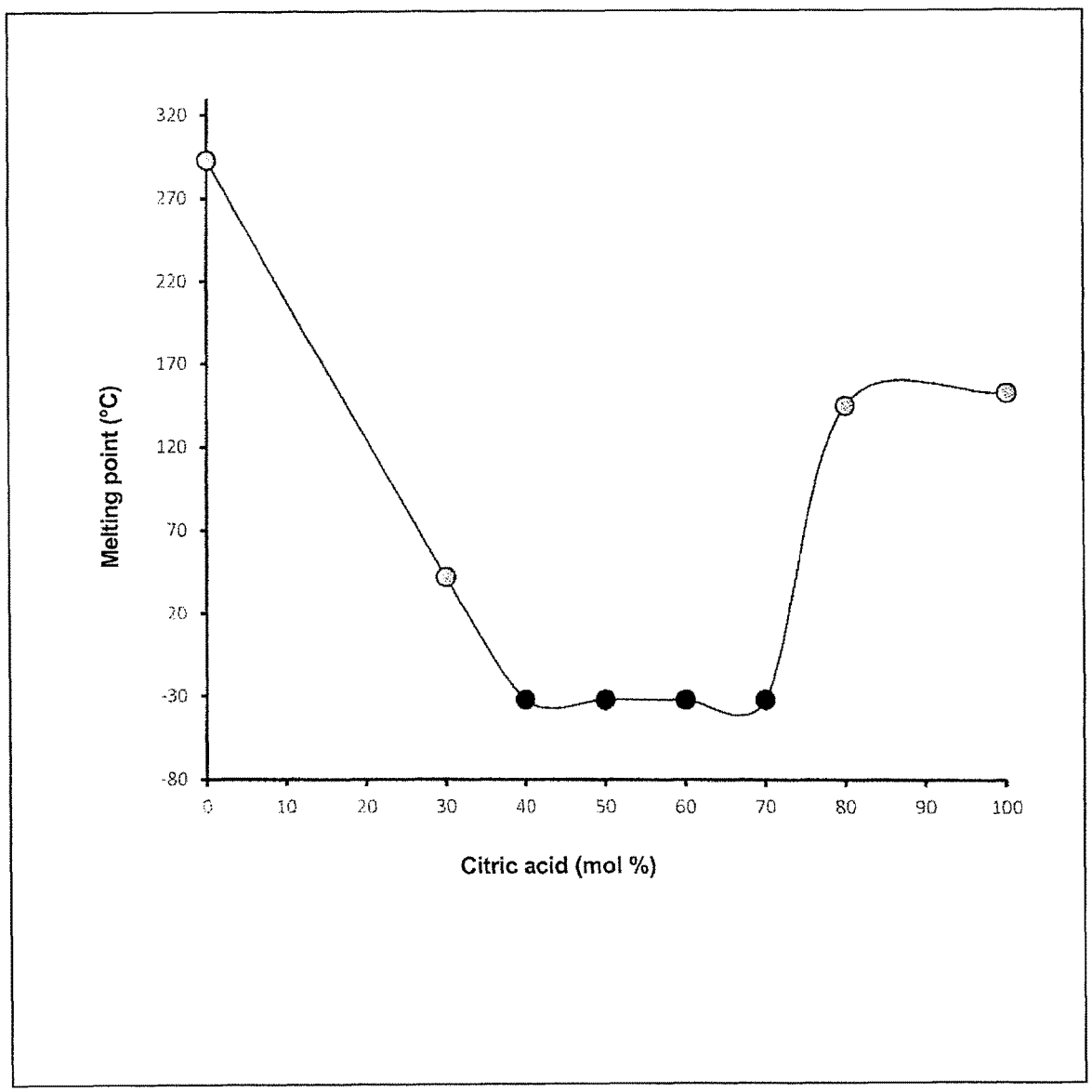
FIG. 3 shows the results obtained from Example 3 as described below as a binary phase diagram between betaine monohydrate and citric acid (hydrogen bond donor). The proportions of betaine monohydrate and citric acid are given in mole %.

Unlike the mixtures described in examples 1 and 2, the betaine:citric acid binary mixtures present no criticality with regard to molar ratio and macroscopic appearance. As can be seen in Table 3, practically all of the composition ranges of the mixture lead to unstable media crystallising after one week. Their use for extraction purposes systematically led to mass setting, either of the mixture alone or of the mixture with the biological material, or even of the liquid extract after filtration. FIG. 3 nevertheless shows that a lowering of the melting point is obtained over a wide composition range compared with pure constituents taken in isolation. By virtue of this fact they satisfy one of the essential criteria of eutectic mixtures. This example not only illustrates the difficulty of obtaining stable eutectic mixtures from betaine, but it also establishes that not all eutectic solvents are suitable for solid/liquid extraction, contrary to what is often suggested in the literature.

Example 4. Test to Obtain Several Eutectic Mixtures and Stability Study at 50° C.

Stability testing, particularly at 50° C., made it possible to highlight the instability and deterioration of certain eutectic mixtures, for example those comprising at least one sugar among glucose, fructose, saccharose and mixtures thereof.

TABLE 4

Stability monitoring of eutectic mixtures including at least one sugar

| Eutectic mixtures (molar ratio) | Visual appearance on formation | Visual appearance after 1 week at 50° C. | Visual appearance after 2 weeks at 50° C. |
| --- | --- | --- | --- |
| Saccharose/glycine/water (1:1:6); (1:1:10) | − | / | / |
| Fructose/glycine/water (1:1:4); (2:1:10) | − | / | / |
| Fructose/choline chloride/water (1:1:4) | + | − | − |
| Fructose/citric acid/water (1:1:6) | + | --- | --- |
| Fructose/lactic acid/water (1:1:6) | + | -- | --- |
| Saccharose/choline chloride/water (1:1:10) | − | / | / |

+: stable, colourless;
−: unstable, crystallisation;
--: unstable, yellow/orange colour;
---: unstable, brown colour

Figure 4:
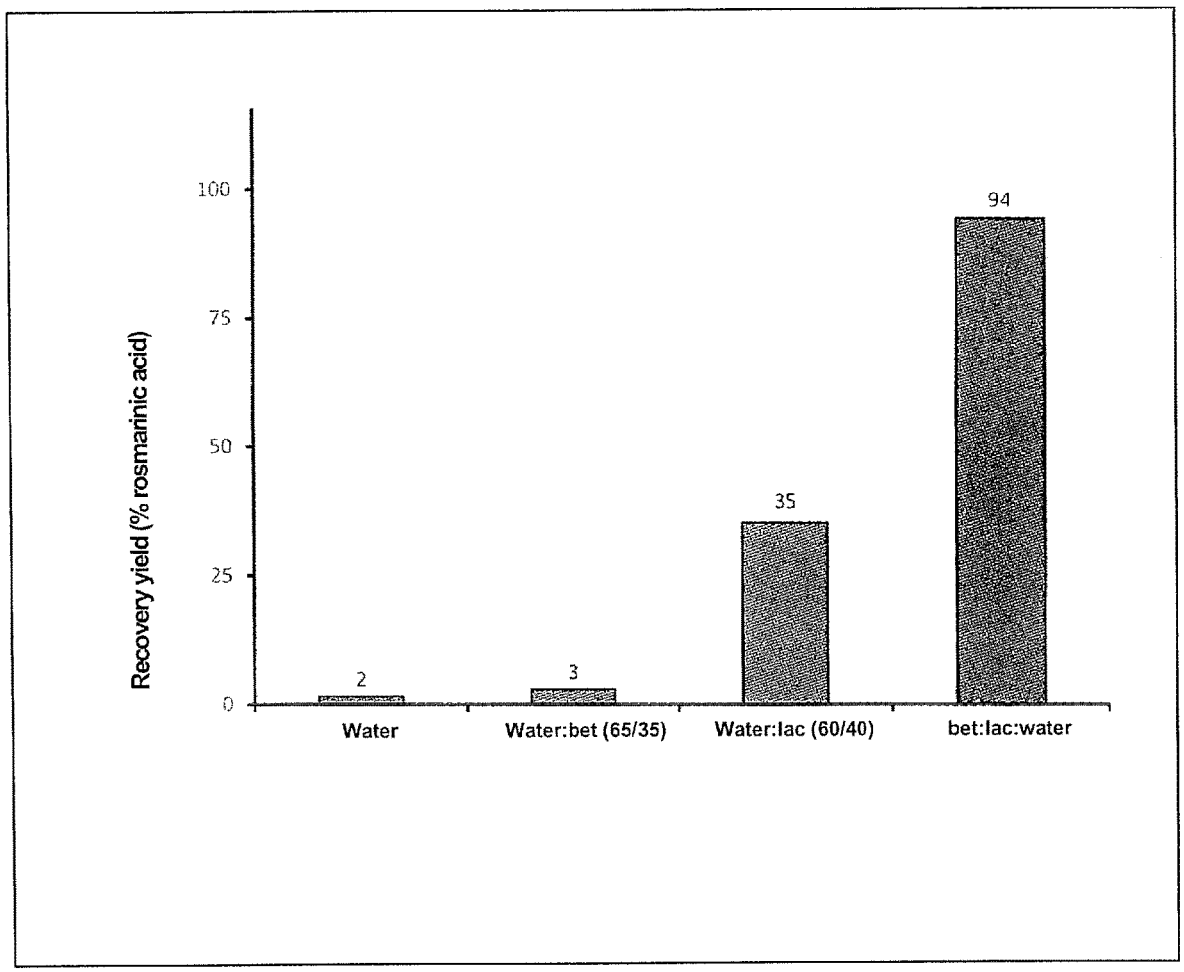
FIG. 4 shows the results obtained from Example 5 as described below as shows the recovery yield of rosmarinic acid depending on the extracting fluid composed of water and/or betaine and/or lactic acid.

Example 5. Influence of Eutectigenesis on the Ability of the Ternary Mixture Betaine:Lactic Acid:Water to Extract Rosmarinic Acid from Rosemary The results presented in this example clearly show the synergy obtained following the formation of the eutectic mixture (FIG. 4). In particular, the recovery rate of rosmarinic acid extracted from rosemary under conditions of maceration at 50° C. for 2 hours in one pass is maximum for the ternary eutectic mixture betaine:lactic acid:water (2:3, mol; 25% by weight of water). The molar ratio between betaine and lactic acid is here equivalent to that for which a eutectic was formed in example 1. The addition of 25% water to the mixture makes it possible to maintain the supramolecular complexes responsible for the synergy while considerably reducing the viscosity of the mixture to facilitate the extraction method. Furthermore, control extractions with water and with water:betaine and water:lactic acid binary mixtures (performed under the same conditions and with the same concentration by weight of betaine or lactic acid) show that the synergy is only obtained when the rosemary is placed in the presence of the eutectic mixture. The latter provides a spectacular improvement in the extraction yield of rosmarinic acid of around 47, 31 and 2.5 times relative to water and to water:betaine and water:lactic acid mixtures, respectively.

Figure 5:
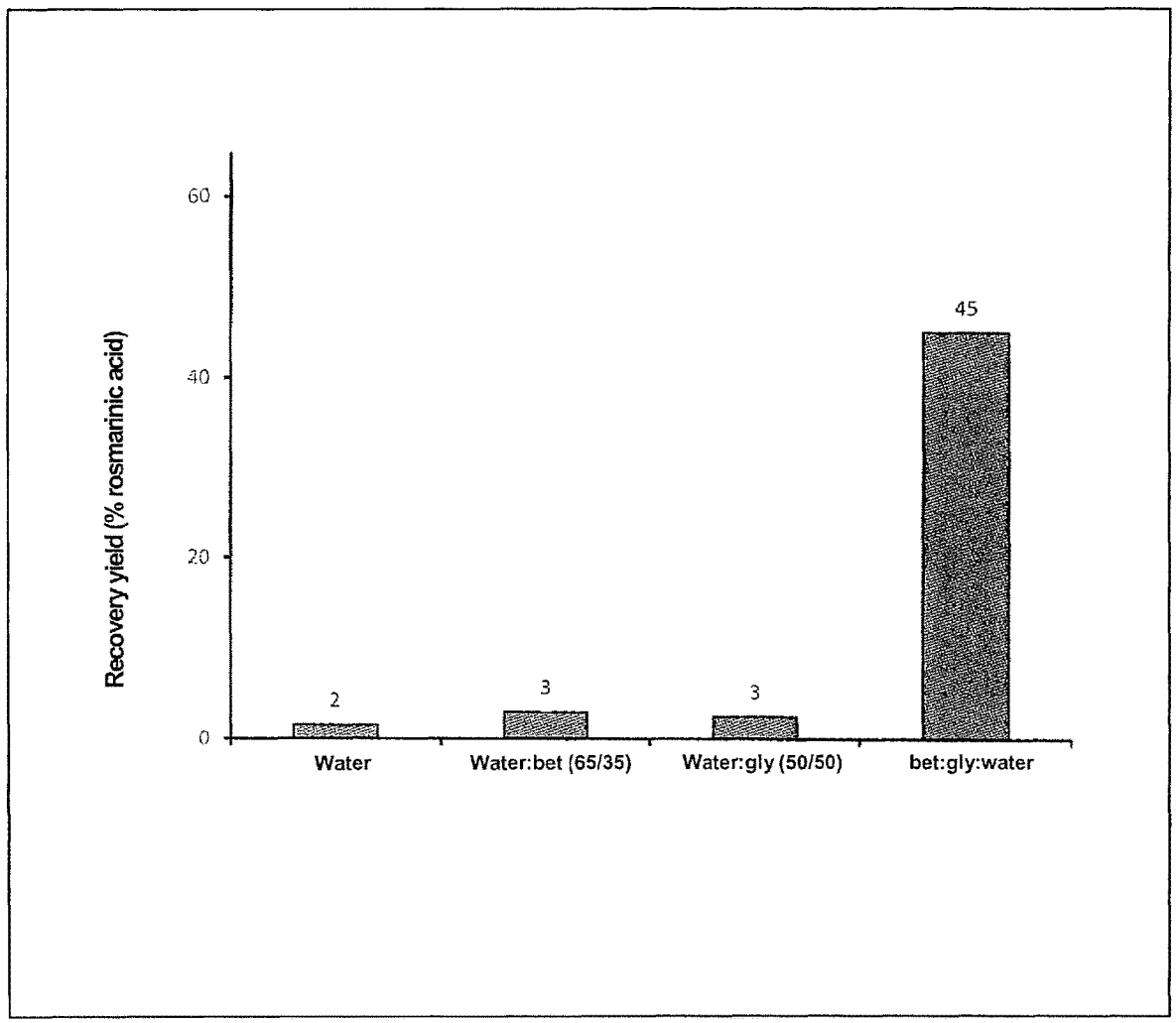
FIG. 5 shows the results obtained from Example 6 as described below as shows the recovery yield of rosmarinic acid depending on the extracting fluid composed of water and/or betaine and/or glycerol.

Example 6. Influence of Eutectigenesis on the Ability of the Ternary Mixture Betaine:Glycerol:Water to Extract Rosmarinic Acid from Rosemary Example 6 shows the synergy obtained with the ternary eutectic mixture of betaine and glycerol (at a molar ratio of 2:3) with 25% by weight of water on the yield of rosmarinic acid extracted from rosemary under maceration conditions at 50° C. for 2 hours (FIG. 5). The molar ratio between betaine and glycerol is equivalent to that for which a eutectic was formed in example 2. The addition of 25% water to the mixture makes it possible to maintain the supramolecular complexes responsible for the synergy while considerably reducing the viscosity of the mixture to facilitate the extraction method. Furthermore, control extractions with water and with water:betaine and water:glycerol binary mixtures (performed under the same conditions and with the same concentration by weight of betaine or glycerol) show that the synergy is only obtained when the rosemary is placed in the presence of the eutectic mixture. The latter provides a spectacular improvement in the extraction yield of rosmarinic acid of around 22 times relative to water and 15 times relative to water:betaine and water:glycerol mixtures, respectively.

Example 7. Comparison of Chemical Profiles and Antioxidant Activity of Rosemary Extracts Obtained Using a Betaine:Lactic Acid:Water Ternary Mixture or a Hydroglycerin Mixture as Extraction Solvent As shown in FIG. 6, the profile of the rosemary extract obtained with the eutectic mixture betaine:lactic acid:water is far richer in diterpenes (141 vs. 8 µg/mL), phenolic compounds (850 vs. 232 µg/m) and rosmarinic acid (340 vs. 3 µg/mL) than that of hydroglycerin extracts. Consequently, eutectic extracts enriched with the compounds of interest, in particular with polyphenolic antioxidants, exhibit an antioxidant activity considerably greater than hydroglycerin extracts (FIG. 7). This activity was determined using a reference test for measuring antioxidant capacity (i.e. the Oxygen Radical Absorbance Capacity or ORAC method).

We note, inter alia, the presence of a high concentration of rosmarinic acid in the eutectic extract of rosemary in question (betaine:lactic acid:water). This molecule presents the particular structural feature of having two catechol cores (ortho-diphenols) which are of optimal molecular structure in terms of antioxidant activity in that they promote the establishment of an intramolecular hydrogen bond between the phenolic hydroxyls. We have also shown in Table 5 that industrial-scale development of this method for obtaining eutectic extracts was possible and, furthermore, yielded results comparable to those observed with the laboratory-scale method, which is an important criterion in terms of the reproducibility of the method claimed in the present invention.

TABLE 5

| Batch | Rosmarinic ac. (µg/mL) | Total diterpenes. (µg/mL) | Phenolics. (µg/mL) |
|---|---|---|---|
| Water:glycerol (50:50; w:w) | 2.7 | 8.1 | 232.1 |
| Betaine:lactic ac (40:60; mol:mol) + water (25% w) (lab scale) | 399.8 | 141.3 | 849.8 |
| Betaine:lactic ac (40:60; mol:mol) + water (25% w) (indus scale) | 327.8 | 156.6 | 784.2 |

Further, the various results show the potential of eutectic extracts of rosemary for cosmetic, food (human and animal), pharmaceutical or nutraceutical applications, as antioxidant agents.

Example 8. Influence of Eutectigenesis on the Ability of the Ternary Mixture Betaine:Glycerol:Water to Extract Oleuropein from Olive Leaves The results presented in this example show the synergy obtained following the formation of the eutectic mixture between betaine and glycerol (for a molar ratio of 2:3) with 25% by weight of water (FIG. 8). The betaine:glycerol molar ratio is equivalent to that for which a eutectic was formed in example 2. The addition of 25% water to the mixture makes it possible to maintain the supramolecular complexes responsible for the synergy while considerably reducing the viscosity of the mixture to facilitate the extraction method. Furthermore, control extractions with water:betaine (65:35, by weight) and water:glycerol (60:40, by weight) binary mixtures, although performed under the same conditions and at the same concentrations by weight, show that the synergy is only obtained when the olive leaves are placed in the presence of the eutectic mixture. The latter provides a spectacular improvement in the recovery of oleuropein (between 2.8 and 9 times) relative to water:betaine and water:glycerol mixtures, and to water, respectively.

Example 9. Influence of Eutectigenesis on the Ability of the Ternary Mixture Betaine:Glycol:Water to Improve the Extraction Efficiency The below experiments of extraction with various glycols were performed. The term <<glycol>> in this example concerns the use of pentylene glycol, propanediol (Zemea®) and propylene glycol. The following extractions, several plant species were used including rosemary leaves, olive leaves, Selaginella pulvinata aerial parts and Tillandsia usnoides aerial parts.

TABLE 6

Olive leaves

| Batch | Oleuropein (µg/mL) |
|---|---|
| Water:propylene glycol (55:45 (2 mol); w:w) | 2000 |
| Betaine:propylene glycol (1:2; mol:mol) + water (20% w) | 3100 |
| Water:propanediol (55:45 (2 mol); w:w) | 1000 |
| Betaine:propanediol (1:2; mol:mol) + water (20% w) | 2800 |
| Water:glycerol (50:50; w:w) | 447.7 |

TABLE 7

Rosemary leaves

| Batch | Rosmarinic acid (µg/mL) |
|---|---|
| Water:propylene glycol (55:45 (2 mol); w:w) | 520 |
| Betaine:propylene glycol (1:2; mol:mol) + water (20% w) | 650 |
| Water:propanediol (55:45 (2 mol); w:w) | 450 |
| Betaine:propanediol (1:2; mol:mol) + water (20% w) | 840 |
| Water:pentylene glycol (50:50 (2 mol); w:w) | 89 |
| Betaine:pentylene glycol (1:2; mol:mol) + water (20% w) | 590 |
| Water:glycerol (50:50; w:w) | 2.7 |

TABLE 8

*Selaginella pulvinata* aerial parts

| Batch | Amentoflavone (µg/mL) |
|---|---|
| Betaine:propylene glycol (1:2; mol:mol) + water (20% w) | 93.7 |
| Betaine:propanediol (1:2; mol:mol) + water (20% w) | 74.3 |
| Betaine:pentylene glycol (1:2; mol:mol) + water (20% w) | 169.0 |
| Water:glycerol (50:50; w:w) | 4.4 |

TABLE 9

*Tillandsia usnoides* aerial parts

| Batch | Total phenolics (µg/mL) |
|---|---|
| Betaine:propanediol (1:2; mol:mol) + water (20% w) | 349.6 |
| Betaine:pentylene glycol (1:2; mol:mol) + water (20% w) | 406.3 |
| Water:glycerol (50:50; w:w) | 324.0 |

Example 10. Comparison of Subcritical Water and Eutectic Mixtures for the Extraction of Oleuropein from Olive Leaves The extraction method by eutectigenesis was compared to a state-of-the-art extractive technology such as subcritical water which consists of an aqueous phase superheated to 125° C. and kept liquid by applying a pressure of 30 to 45 bars. FIG. 9 shows that ternary eutectic mixtures composed of betaine and lactic acid or glycerol (2:3, mol) with 25% by weight of water yield more oleuropein from a plant (e.g.

vegetable) matrix such as olive leaves than subcritical water. This result is interesting in that oleuropein, like most phenolic compounds, is heat sensitive and therefore subject to thermo-oxidation. Furthermore, from the standpoint of eco-extraction and green chemistry, it is advantageous to lower both the temperature and the pressure of the process with a view to saving energy and putting into effect environmentally friendly processes.

Example 11. Comparison of Chemical Profiles and Biological Activity of Olive Leaf Extracts Obtained Using a Betaine:Glycerol:Water Ternary Mixture or a Hydroglycerin Mixture as Extraction Solvent The chromatographic profiles shown in FIG. 10 indicate the higher plant (e.g. vegetable) actives concentration of eutectic extracts (betaine:glycerol:water) compared with hydroglycerin extracts. This result is particularly striking for oleuropein. At the laboratory scale, the addition of betaine in a water:glycerol mixture makes it possible, by virtue of the phenomenon of eutectigenesis shown in Example 2—to triple (or quadruple) the concentration of oleuropein. When the extraction process by eutectigenesis is transferred to the industrial scale (as shown in Table 10), this increase even reaches a factor of 5.4. In a similar manner, the total content of phenolic compounds is 2.6 and 3.4 times greater for eutectic extracts of olive leaves respectively obtained at the laboratory and industrial scale than for conventional liquid extracts using a water:glycerol mixture (50:50; w:w).

TABLE 10

| Batch | Oleuropein (µg/mL) | Total phenolics. (µg/mL) |
|---|---|---|
| Water:glycerol (50:50; w:w) | 447.7 | 894.8 |
| Betaine:glycerol (40:60; mol:mol) + water (25% w) (lab scale) | 1721.6 | 2367.1 |
| Betaine:glycerol (40:60; mol:mol) + water (25% w) (indus scale) | 2303.3 | 3017.2 |

These results can be taken as explaining the spectacular increase in collagen synthesis on human skin fibroblasts (FIG. 11A) and photo-protection on Hacat cells (FIG. 11B) following the incubation of eutectic extracts of olive leaves in concentrations ranging from 0.01 to 0.1%. For example, an aqueous formulation of eutectic extract at 0.1% is 18 times more active in terms of collagen synthesis than the same formulation using a hydroglycerin extract. This improved efficacy therefore makes it possible to lower the required concentrations of eutectic extracts, which presents a certain number of advantages. Specifically, when a ten times less concentrated formulation of eutectic extracts is used (0.01%), its biological efficacy relative to the gain in collagen in the extracellular matrix is equivalent to, and often even greater than, hydroglycerin extracts that are ten times more concentrated. Furthermore, in terms of preventive photo-protection—treatment of cells with extracts before UVA irradiation—shown in FIG. 11B, we see a factor 4.7 increase in biological activity, which is considerable.

These data illustrate the potential of eutectic extracts as photo-protective agents, UV filters, anti-ageing and hydrating agents (collagen has the property of retaining water and also performs a barrier function for the skin). Also, given the known antioxidant activity of oleuropein (Laguerre et al., Characterization of olive leaf phenolics by ESI-MS and evaluation of their antioxidant capacities by CAT assay, J. Am. Oil Chem. Soc. 2009, 86, 1215-1225), the chromatographic profiles presented in FIG. 10 point to the possibility of using these improved extracts as antioxidants in various formulations.

Example 12. Comparison of Chemical Profiles and Biological Activity of Cherry Blossom Extracts Obtained Using Betaine:Glycerol:Water and Betaine:Lactic Acid:Water Ternary Mixtures or a Hydroglycerin Mixture as Extraction Solvents The results presented in this example perfectly illustrate the fact that the use of the eutectic solvents claimed in the present invention for extracting plant (e.g. vegetable) substances make is possible to obtain extracts "unattainable" by conventional solvents of the water:glycerol type. This applies especially to the chromatographic profile shown in FIG. 12 and data shown in Table 11 between an extraction with a eutectic mixture and a hydroglycerin mixture. The extracts are totally different. Extraction by eutectigenesis makes it possible in this case to generate a novel cherry blossom extract including numerous new compounds (compared with conventional extracts) such as chlorogenic acid identified by mass spectrometry or a glucoside of coumaric acid, rutin, dicaffeoylquinic acid or isorhamnetin. In quantitative terms, a dramatic increase in the content of polyphenols was recorded for the eutectic solvents betaine:glycerol:water and betaine:lactic acid:water compared with hydroglycerin extracts (4.3 and 13.7 times more concentrated, respectively).

TABLE 11

| Batch | Caffeoyl glucoside (µg/mL) | Total phenolics. (µg/mL) |
|---|---|---|
| Water:glycerol (50:50) | nd | 45.58 |
| Betaine:lactic ac. (40:60; mol:mol) + water (25% w) | 332.68 | 625.55 |
| Betaine:glycerol (40:60; mol:mol) + water (25% w) | 63.94 | 196.99 |

Figure 13:
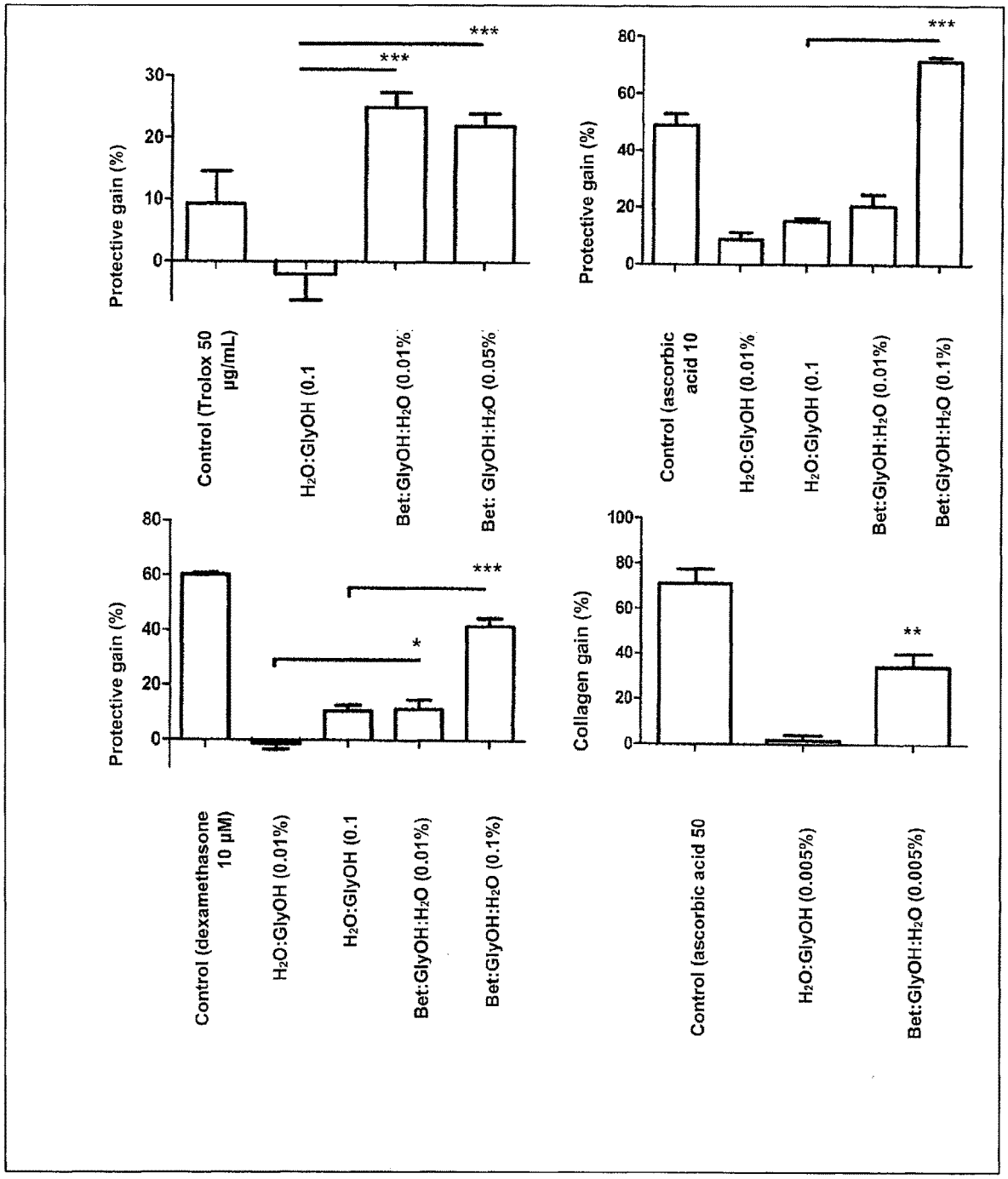
Figure 14:
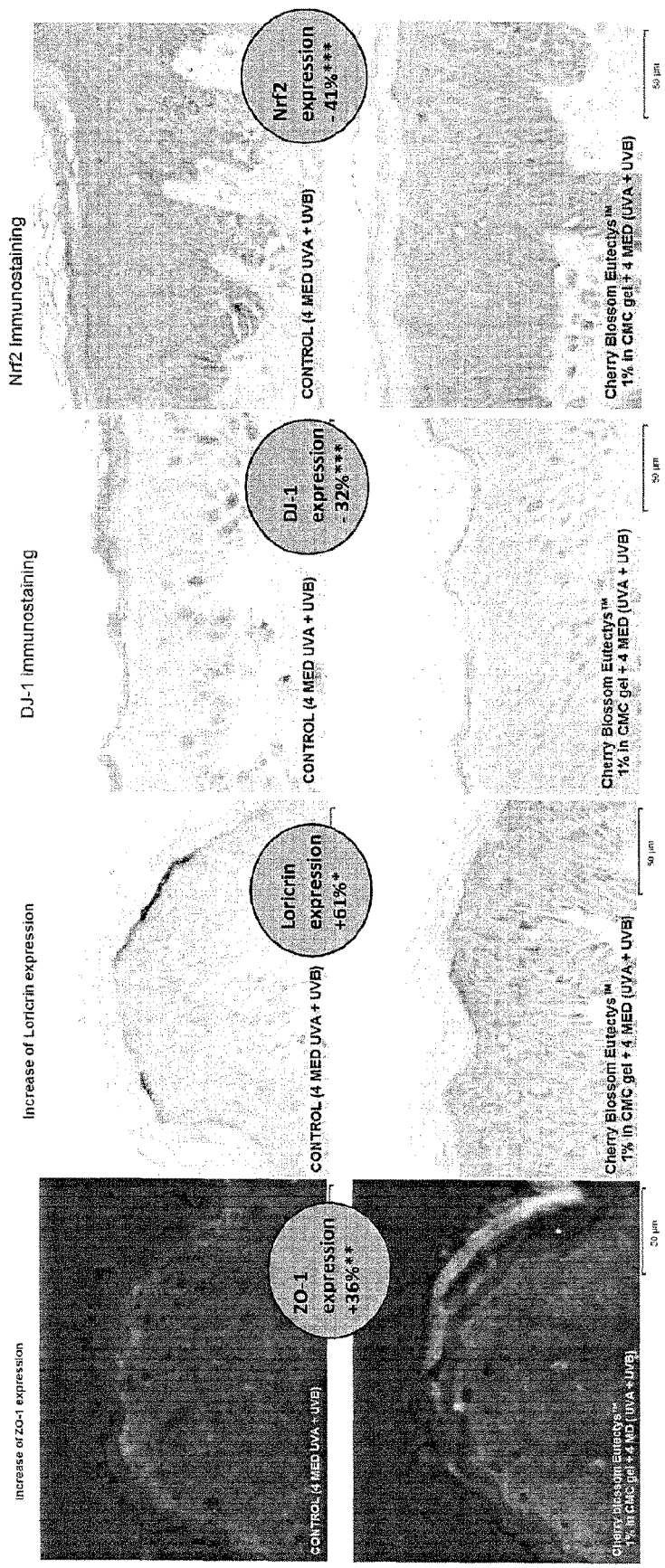

With regard to biological activity, the eutectic extracts once again show a spectacular superiority in terms of photo-protection, type 1 matrix metalloproteinase (MMP-1) inhibition, anti-inflammatory activity and collagen synthesis. Only the results for extracts obtained from a betaine:glycerol:water mixture are presented here, although similar data were recorded for the betaine:lactic acid:water mixture. As shown in FIG. 13A, eutectic extracts are far more active than hydroglycerin extracts as photo-protective agents; it may even be said that the latter extracts are devoid of all efficacy. A similar conclusion can also be made on the basis of the results obtained for the inhibition of type 1 extracellular matrix metalloproteinases (MMP-1) involved in photo-ageing (FIG. 13B), for the inhibition of TNFα which marks an important inflammation pathway (FIG. 13C), and also for the synthesis of collagen soluble in the extracellular matrix (FIG. 13D). Moreover, based on an UV-induced Human skin explant model, the cherry blossom eutectic extract is able to increase the tight junction protein ZO-1 (Zona occuldens) and loricrin synthesis involved in the skin barrier function, cell adhesion and cohesion leading to skin hydration (FIGS. 14A and 14B) but also have an antioxidant activity as the skin cells do not need to recruit the DJ-1/NRF2 pathway to fight against UV damage (FIGS. 14C and 14D). For each of these activities, very significant quantitative gains were obtained using the solvents and the extraction methods claimed in the present invention.

These results open the way to novel applications for these extracts as anti-inflammatory, soothing, anti-ageing, photoprotective and antioxidant agents, UV filters, hydrating agents, or anti-photo-ageing agents.

Example 13. Comparison of Chemical Profiles and Biological and Physico-Chemical Activity of Horsetail Extracts Obtained Using a Betaine:Lactic Acid:Water Ternary Mixture or a Hydroglycerin Mixture as Extraction Solvent Like cherry blossom, the example of horsetail illustrates the fact that extraction by eutectigenesis provides a means of obtaining novel extracts. FIG. 15 compares two chromatographic traces of which it may be said, at the very least, that they are not superimposed on one another. Among other differences we can mention that kaempferol dihexoside rhamnoside, gossypitrin, protogenkwanin-4'-O-glucoside and phaseolic acid are present at higher concentrations in the eutectic extract (betaine:lactic acid:water) compared with the hydroglycerin extract. Table 12 also demonstrates the differences in the phenolic content of the extracts obtained.

TABLE 12

| Batch | Total phenolics (µg/mL) |
|---|---|
| Water:glycerol (50:50; w:w) | 395.1 |
| Betaine:lactic ac. (40:60; mol:mol) + water (25% w) | 387.4 |

It is nevertheless difficult to reach a conclusion as to the superiority of such and such an extract solely on the basis of profiles as differentiated as these. For this reason biological activity tests were carried out on the inhibitory action of natural substances extracted from horsetail on the pro-inflammatory cascade leading to the production of TNFα (FIG. 16). For an equivalent concentration by weight (0.01%), it is clearly apparent that the eutectic extract of horsetail is more active than that derived from a simple water:glycerol mixture. A dose-response is also found, which is advantageous for adjusting the formulation depending on the level biological efficacy sought after. Overall, the activity increases by a factor 5 when the concentration is increased by a factor 10. An comparative analysis of antioxidant activity between the extracts was also carried out. FIG. 17 shows a factor 1.6 greater efficacy in reducing peroxyradicals derived from an azo initiator for the eutectic extract of horsetail compared with the hydroglycerin extract.

Eutectic extracts of horsetail therefore appear promising for applications as anti-inflammatory and antioxidant agents in a large number of fields (principally pharmaceutical, nutraceutical and cosmetic). With regard to the cosmetics field, these extracts can be used as soothing agents (via their anti-TNFα properties) and as antioxidant and anti-ageing agents (via their free radical reducing properties).

Example 14. Comparison of Chemical Profiles and Biological Activity of Crithmum (Rock Samphire) Extracts Obtained Using a Betaine:Glycerol:Water Ternary Mixture or a Hydroglycerin Mixture as Extraction Solvent At first sight, of all the chromatographic profiles presented herein, the profiles for chrismum are the least differentiated between the extractive approach by eutectigenesis and that employing conventional solvents such as water and glycerol (50:50; w:w). In terms of phenolic compounds, the two extracts are equivalent overall with concentrations of 195 and 181 µg/mL respectively for hydroglycerin and eutectic extracts (FIG. 18). Table 13 also demonstrates the differences in the total phenolic compounds obtained.

TABLE 13

| Batch | Total phenolics (µg/mL) |
|---|---|
| Water glycerol (50:50; w:w) | 195.07 |
| Betaine:glycerol (40:60; mol:mol) + water (25% w) | 181.2 |

The eutectic extract contains less 1-caffeoylquinic and 5-coumaroylquinic acids, but more dicaffeoylquinic and 5-feruloylquinic acid than the extract with water and glycerol. However, for other compounds, such as 5-caffeoylquinic acid, the two extracts present substantially similar concentrations. Because these different molecules have phenolic cores that differ in number (one or two cycles per molecule) and in structure (ferulic vs. coumaric vs. caffeic), variations in the profiles, even of an apparently modest nature, can engender very marked differences in biological and/or physico-chemical activity. This can be seen in FIG. 19 where an aqueous formulation of a eutectic extract of chrismum at 0.1% shows an inhibition of melanin synthesis on human epidermal melanocytes (lightly pigmented) of 33%, whereas the hydroglycerin extract is devoid of all activity.

This is an important result inasmuch as arbutin—which is the natural hypo-pigmenting agent most widely used in cosmetics—releases a toxic compound (hydroquinone) (ref). This a favourable context for the development of novel bleaching agents that are both natural and free of arbutin. In this sense, the results presented in this example fully demonstrate the potential of the eutectic extracts of chrismum claimed in this invention for applications in skin bleaching. Furthermore, by virtue of the established responsiveness of the catechol cores of quinic esters of hydroxycinamic acids (caffeic, ferulic, coumaric, etc.) present in the eutectic extracts, the latter are all indicated for applications in the cosmetic, nutraceutical, pharmaceutical or food industry as antioxidants.

Example 15. Comparison of Chemical Profiles of Plantain Extracts Obtained Using a Betaine:Glycerol:Water Ternary Mixture or a Hydroglycerin Mixture as Extraction Solvent Example 15 demonstrates the fact that the extraction using a betaine:glycerol:water eutectic mixture produces a chromatographic profile richer overall in total verbascosides compared with that of the hydroglycerin extract (FIG. 20). The total verbascosides concentration increases from 197 to 397 µg/mL (that is double) by adding betaine to the water-glycerol mixture (as shown in Table 14). In this instance, compound 6—verbascoside—is a very powerful antioxidant (Laguerre et al., 2009) containing two catechol cores—like the rosmarinic acid presented in Examples 6 and 7.

TABLE 14

| Batch | Total Verbascosides (µg/mL) | Total Phenolics (µg/mL) |
|---|---|---|
| Water:glycerol (50:50; w:w) | 197.1 | 211.2 |
| Betaine:glycerol (40:60; mol:mol) + water (25% w) (lab scale) | 397 | 486.4 |
| Betaine glycerol (40:60; mol:mol) + water (25% w) (indus scale) | 646.7 | 842.1 |

More precisely, it is a heterosidic ester of caffeic acid and hydroxytyrosol involved in a large number of biological and/or physico-chemical activities. Furthermore, in a spectacular manner, adaptation of the extraction method to the industrial scale makes it possible to increase the total verbascosides content by more than three times and that of phenolic compounds by nearly double. Also, a comparison of total phenolic compounds between the eutectic extract of plantain obtained at the laboratory scale and the hydroglycerin extract shows a factor 2.3 difference in favour of the eutectic extract.

Example 16. Comparison of Chemical Profiles of Saffron Flower Extracts Obtained Using a Betaine:Lactic Acid:Water Ternary Mixture or a Hydroglycerin Mixture as Extraction Solvent The chromatographic profiles shown in FIG. 21 differ mainly in terms of the presence of kaempferol glycosyl-glyceryl rhamnoside and of two isomers of kaempferol-3-O-lactyl sophoroside (as shown in Table 15).

TABLE 15

| Batch | Crocins (µg/mL) | Total flavonoids (µg/mL) |
|---|---|---|
| Water:glycerol (50:50; w:w) | 14.43 | 2349 |
| Betaine:lactic ac. (40:60; mol:mol) + water (25% w) (lab scale) | 6.35 | 2414 |

These active constituents of saffron flowers were able to be identified by liquid chromatography-electrospray ionization-tandem mass spectrometry (LC-ESI/MS). They are virtually absent from the profiles obtained from the hydroglycerin extract, which could explain the results given in FIG. 22 showing an increased efficacy of the eutectic extract on the inhibition of melanin synthesis and on the release of mtalloproteinases in the extracellular matrix—albeit in a more modest manner in the latter case. If it is assumed that the flavonoid fraction is the only one involved in the biochemical determinism of these two activities, it may then be suggested that the presence of kaempferol glycosyl-glyceryl rhamnoside and of isomeric forms of kaempferol-3-O-lactyl sophoroside is of prime importance for obtaining extracts endowed with increased biological activity relative to conventional extracts of the hydroglycerin type. These results also demonstrate the potential of eutectic extracts of saffron flowers as hypo-pigmenting, photo-protective and anti-ageing agents. Furthermore, given the chemical nature of the molecules of which they are composed (flavonoids), these eutectic extracts bode well for higher free radical stabilising activities than those of conventional extracts, and hence use thereof as antioxidants.

Example 17. Comparison of Chemical Profiles of Rose of Jericho Extracts Obtained Using Betaine:Glycerol:Water and Betaine:Lactic Acid:Water Ternary Mixtures or a Hydroglycerin Mixture as Extraction Solvents The extracts obtained from an extraction by eutectigenesis (whether it be betaine:glycerol:water or betaine:lactic acid:water) present profiles totally different from those observed by chromatography and derived from a water and glycerin extraction (FIG. 23). These data demonstrate the differentiating character induced by the use of deep eutectic solvents such as claimed in the present invention in comparison with a more conventional method. In this instance, the eutectic extract shown in FIG. 23 contains far more taxifolin (and its methyl ether), protocatechic acid and flavonolignans such as sylibin and isosylibin (as shown in Table 16). It is interesting to note that the total concentration of phenolic compounds is respectively 2 and 3 times higher for extracts derived from the use of betaine:lactic acid:water and betaine:glycerol:water mixtures than for the use of a water:glycerol mixture.

TABLE 16

| Batch | Taxifolin (µg/mL) | phenolics (µg/mL) |
|---|---|---|
| Water:glycerol (50:50; w:w) | 14.4 | 28.03 |
| Betaine:glycerol (40:60; jmol:mol) + water (25% w) | 25.8 | 83.9 |
| Betaine:lactic ac. (40:60; mol:mol) + water (25% w) | 28.3 | 53.8 |

In terms of biological activity, the eutectic extract of which the chromatographic profile is shown in FIG. 23 (betaine:glycerol:water) inhibits melanin synthesis by nearly 36%, whereas the hydroglycerin extract is devoid of all activity (FIG. 24). This is a logical result given the profile, taxifolin being known to inhibit cellular melanogenesis (An et al., Flavonoids, taxifolin and luteolin attenuate cellular melanogenesis despite increasing tyrosine protein levels, Phytother. Res. 2008, 22, 1200-1207), as effectively in fact as arbutin which is widely used in cosmetics as a hypo-pigmenting agent. On this point, it should be pointed out that arbutin is not a satisfactory active as it releases hydroquinone, the presence of which is prohibited (particularly in cosmetics over 1 ppm). This type of activity in the absence of arbutin thus demonstrates the great potential of the eutectic extract of rose of Jericho for the cosmetics sector, in the range of hypo-pigmenting agents, but also as antioxidant and anti-ageing agents given that protocatechic acid and taxifolin are effective free radical reducers, each having a catechol core of which the mechanism of action in controlling oxidative stress has been explained hereinabove. Finally, example 17 demonstrates the fact that eutectic solvents are perfectly suited to the extraction of bio- or chemo-active compounds from resurrection plants.

The invention claimed is:
1. A eutectic extraction solvent for extracting plant and/or animal and/or prokaryotic biological material, wherein the eutectic extraction solvent is a clear, stable and fluid mixture consisting essentially of:
    (a) betaine (trimethyl glycine) or a hydrated form of betaine;
    (b) glycerol; and
    (c) water;

wherein the molar ratio of betaine or a hydrated form of betaine to glycerol is from 1:1.5 to 1:3 and the proportion of water added to the mixture is from 20 to 30% by weight;

with the proviso that the eutectic extraction solvent does not contain any exogenous sugar, or amine salt or anion.

2. A eutectic extraction solvent according to claim 1, wherein the molar ratio of betaine or a hydrated form of betaine to glycerol is from 1:2 to 1:3.

3. A method for extracting natural biological compounds from plant biological material, wherein the method comprises the following steps:
   a. immersing, while stirring, a ground or unground biological material in a eutectic extraction solvent as defined in claim 1; then
   b. macerating or percolating or infusing the mixture obtained in step a. at a temperature between 20 and 60° C.; then
   c. filtering the extraction product obtained at step b., thereby obtaining a natural biological liquid extract derived from the plant and/or animal and/or prokaryotic biological material.

4. The method according to claim 3, wherein the plant biological material is selected from the group consisting of cherry blossom, horsetail, plantain, saffron flowers, chrismum, rose of Jerico, rosemary, Selaginella *pulvinata*, Tillandsia usnoides and olive leaves.

5. A natural biological liquid extract comprising plant biological material obtained by the extraction method according to claim 4, wherein the eutectic extraction solvent is present in the liquid extract in an amount of from about 0.01 to about 50% by weight.

6. The method according to claim 3, wherein the extraction product obtained at step c. comprises one or more biological compounds selected from the group of phenolic compounds including phenolic acids and esters, flavonoids, secoiridoids, stilbenes and phenolic alcohols, antioxidants, carotenoids, alkaloids, lipids, phenylpropanoids, flavourings and taste modifiers, fragrances, biocides, antimicrobials, proteins, enzymes, colourings, pigments, surfactants and terpenoids including saponins.

7. The method according to claim 3, wherein the temperature in step b is from about 25° C. to about 45° C.

8. A natural biological liquid extract comprising plant biological material obtained by the extraction method according to claim 3, wherein the eutectic extraction solvent is present in the liquid extract in an amount of from about 0.01 to about 50% by weight.

9. The liquid extract according to claim 8, wherein the eutectic extraction solvent is present in the liquid extract in an amount of from about 0.1 to about 25% by weight.

10. The liquid extract according to claim 8, wherein the liquid extract comprises biological compounds extracted from plant biological material selected from the group consisting of cherry blossom, horsetail, plantain, saffron flowers, chrismum, rose of Jerico, rosemary, olive leaves, Selaginella *pulvinata* and Tillandsia usnoides.

11. A pharmaceutical composition comprising a liquid extract according to claim 10.

12. A natural biological liquid extract derived from cherry blossom according to claim 10.

13. A pharmaceutical composition comprising a liquid extract according to claim 8.

14. The pharmaceutical composition according to claim 13, wherein the composition is suitable for oral or parenteral administration, or for topical, rectal, nasal, auricular, vaginal and/or ocular application.

* * * * *

UNITED STATES PATENT AND TRADEMARK OFFICE
CERTIFICATE OF CORRECTION

Page 1 of 1

PATENT NO. : 10,960,042 B2
APPLICATION NO. : 15/564985
DATED : March 30, 2021
INVENTOR(S) : Lavaud et al.

It is certified that error appears in the above-identified patent and that said Letters Patent is hereby corrected as shown below:

In the Claims

Claim 3, Column 35, Line 22, delete "and/or animal and/or prokaryotic".

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*